United States Patent
Junker et al.

(10) Patent No.: US 6,645,178 B1
(45) Date of Patent: Nov. 11, 2003

(54) APPARATUS FOR INSERTING MEDICAL DEVICE

(76) Inventors: Larry G. Junker, 8930 Roam La. East, Inverness, FL (US) 34450; John D. Thorniley, 3277 E. Dorchester Dr., Palm Harbor, FL (US) 34684

( * ) Notice: Subject to any disclaimer, the term of this patent is extended or adjusted under 35 U.S.C. 154(b) by 0 days.

(21) Appl. No.: 09/200,113

(22) Filed: Nov. 25, 1998

Related U.S. Application Data

(63) Continuation-in-part of application No. 08/790,708, filed on Apr. 21, 1997, now abandoned.

(51) Int. Cl.[7] .............................................. A61M 5/178
(52) U.S. Cl. ................................................. 604/164.05
(58) Field of Search ................................ 604/164, 170, 604/161, 165, 162, 160, 171, 264, 523, 164.01, 164.04, 164.05, 164.06, 164.07, 170.01, 170.02, 170.03, 165.01

(56) References Cited

U.S. PATENT DOCUMENTS

| | | | |
|---|---|---|---|
| 1,064,307 A | | 6/1913 | Fleming |
| 2,566,499 A | | 9/1951 | Richter |
| 4,529,399 A | * | 7/1985 | Groshong et al. ............ 604/53 |
| 4,747,833 A | | 5/1988 | Kousai et al. |
| 4,772,266 A | | 9/1988 | Groshong |
| 4,840,613 A | | 6/1989 | Balbierz |
| 5,098,392 A | | 3/1992 | Fleischhacker et al. |
| 5,125,902 A | * | 6/1992 | Berry et al. ................. 604/164 |
| 5,125,904 A | | 6/1992 | Lee |
| 5,154,703 A | | 10/1992 | Bonaldo |
| 5,167,634 A | * | 12/1992 | Corrigan, Jr. et al. ...... 604/160 |
| 5,292,311 A | * | 3/1994 | Cope .......................... 604/165 |
| 5,312,355 A | | 5/1994 | Lee |
| 5,380,292 A | | 1/1995 | Wilson |
| 5,397,311 A | | 3/1995 | Walker et al. |
| 5,584,820 A | | 12/1996 | Gurmarnik |
| 5,613,953 A | | 3/1997 | Pohndorf |

* cited by examiner

Primary Examiner—John G. Weiss
Assistant Examiner—Ann Y Lam
(74) Attorney, Agent, or Firm—Frijouf, Rust & Pyle, P.A

(57) ABSTRACT

An apparatus is disclosed for inserting a medical device such as a catheter into a patient. The apparatus comprises a rigid obturator defining a distal obturator end. A flexible sheath has an internal bore terminating at a distal sheath end. The internal bore of the sheath receives the obturator for supporting the sheath to enable insertion of the sheath within the patient. The obturator is advanced relative to the sheath to fracture the distal sheath end. The obturator is removed from the sheath for enabling the medical device to be inserted through the sheath to enter into the patient. The sheath is removed from the patient while the medical device remains within the patient.

20 Claims, 18 Drawing Sheets

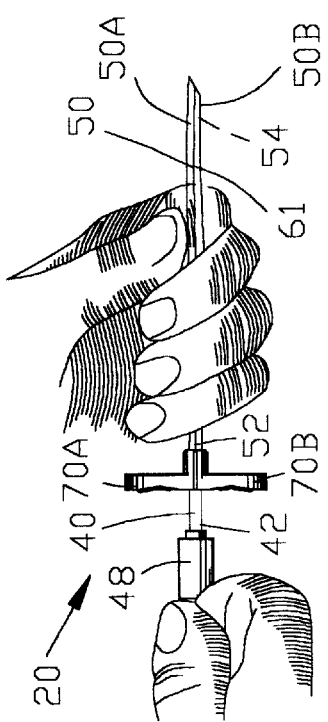
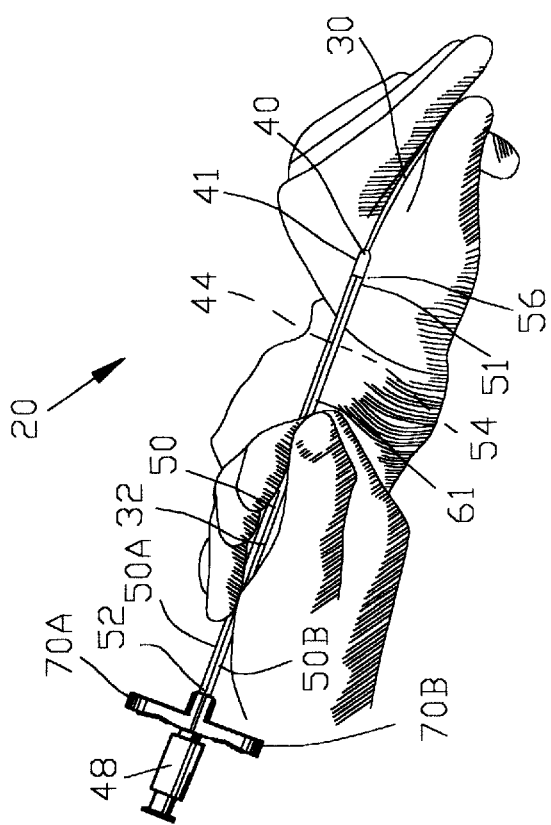
FIG. 4
FIG. 3

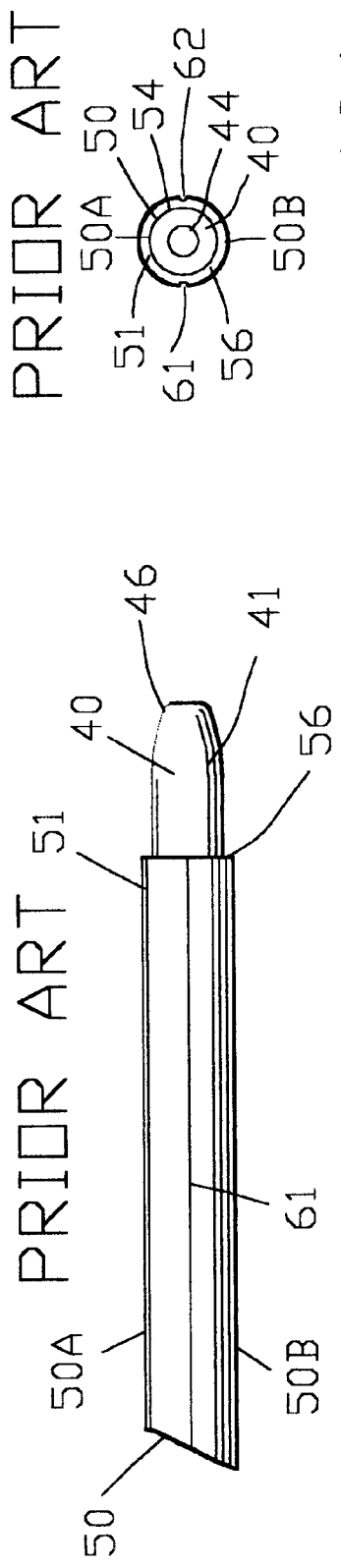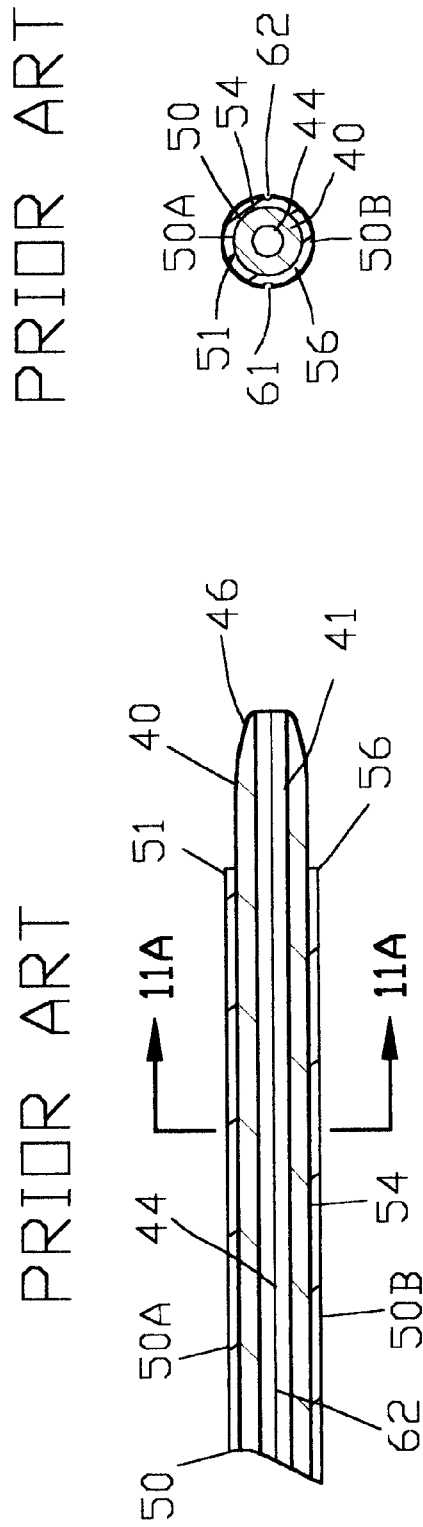

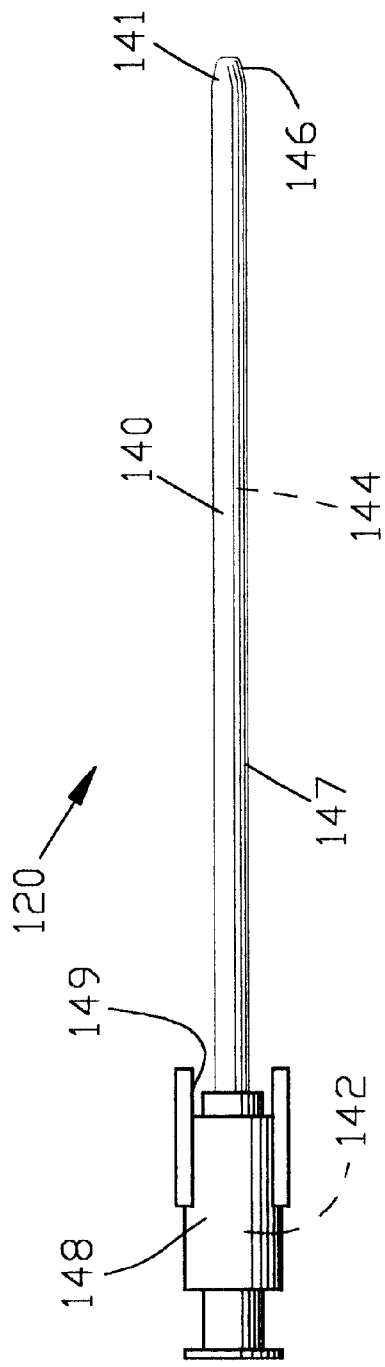
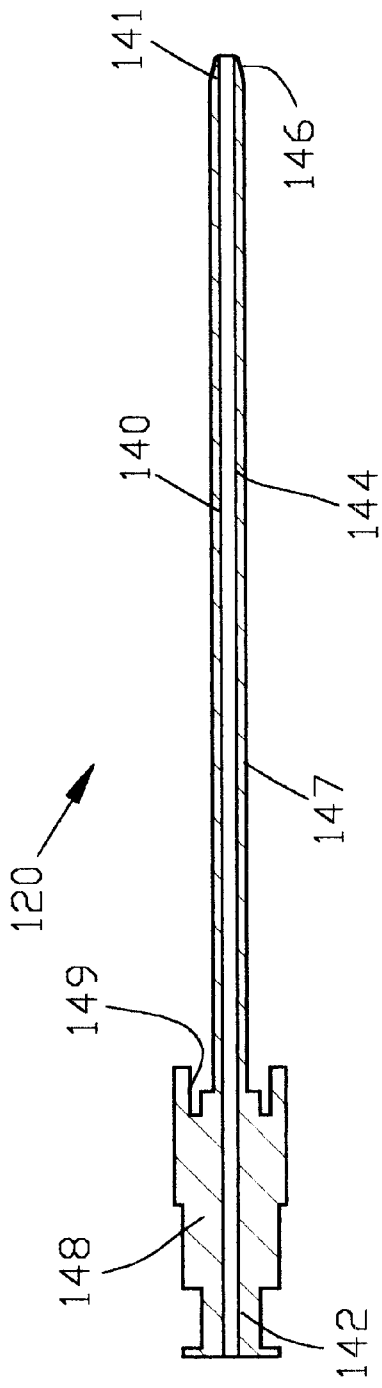

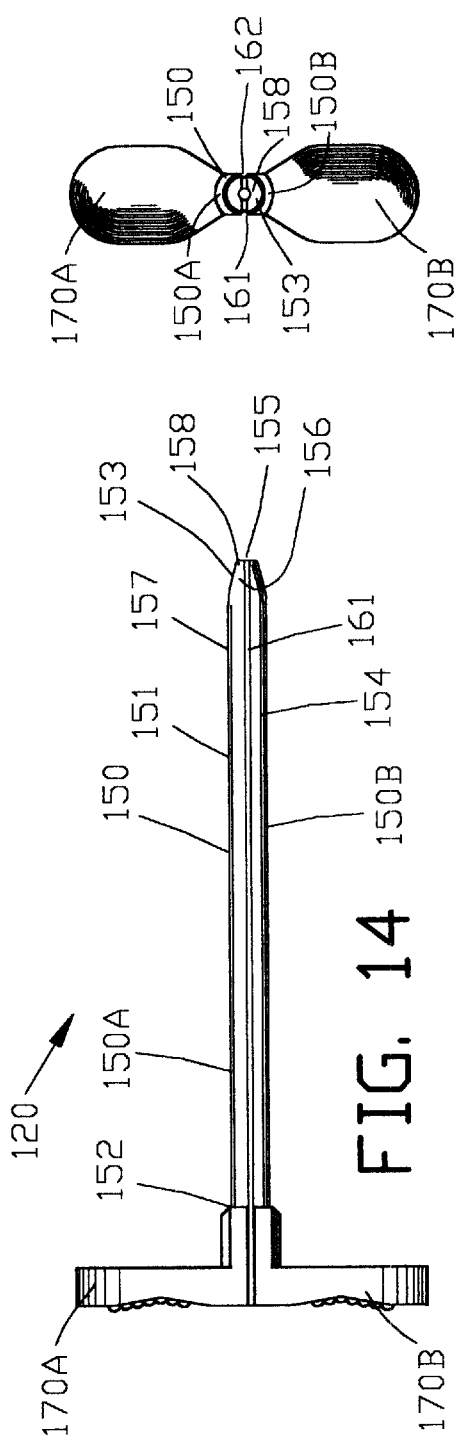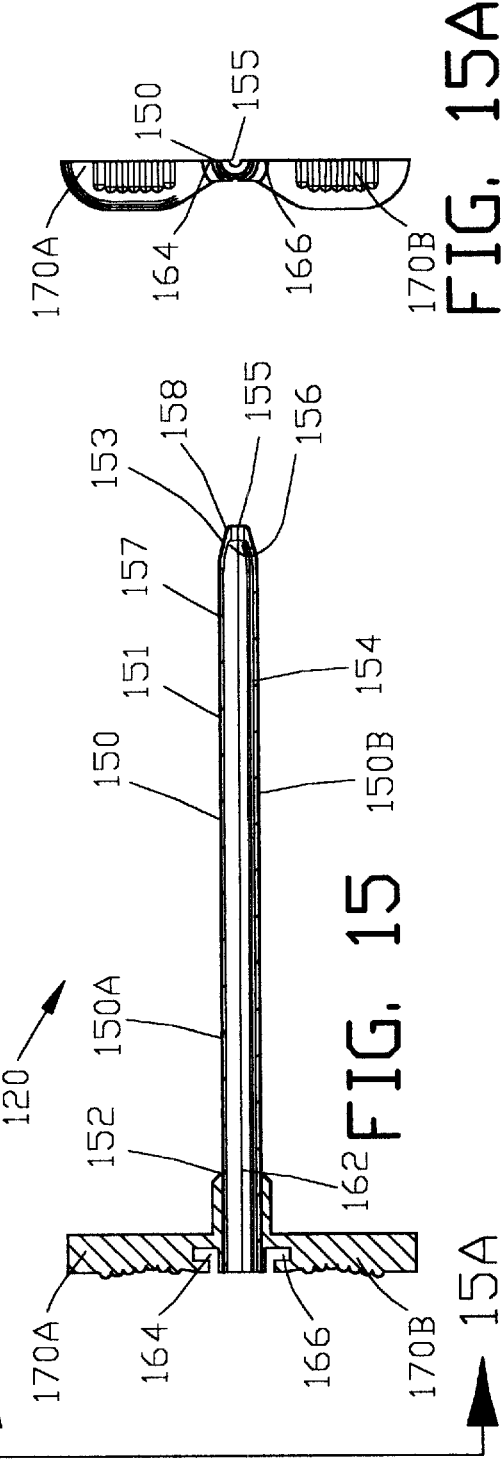

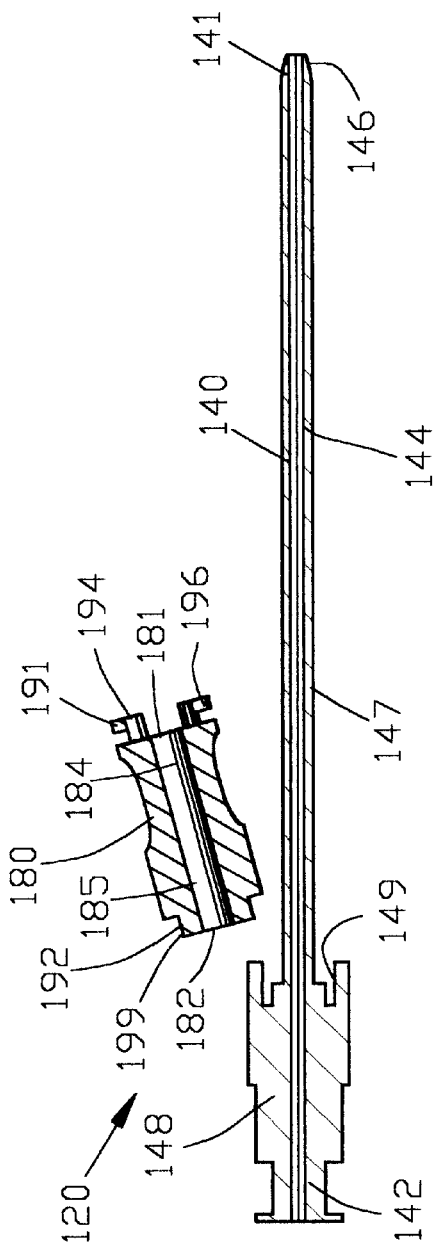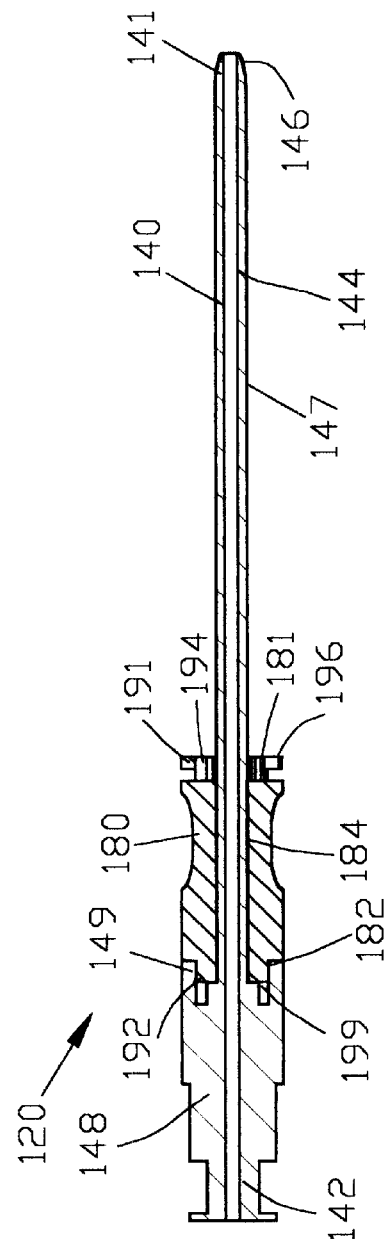

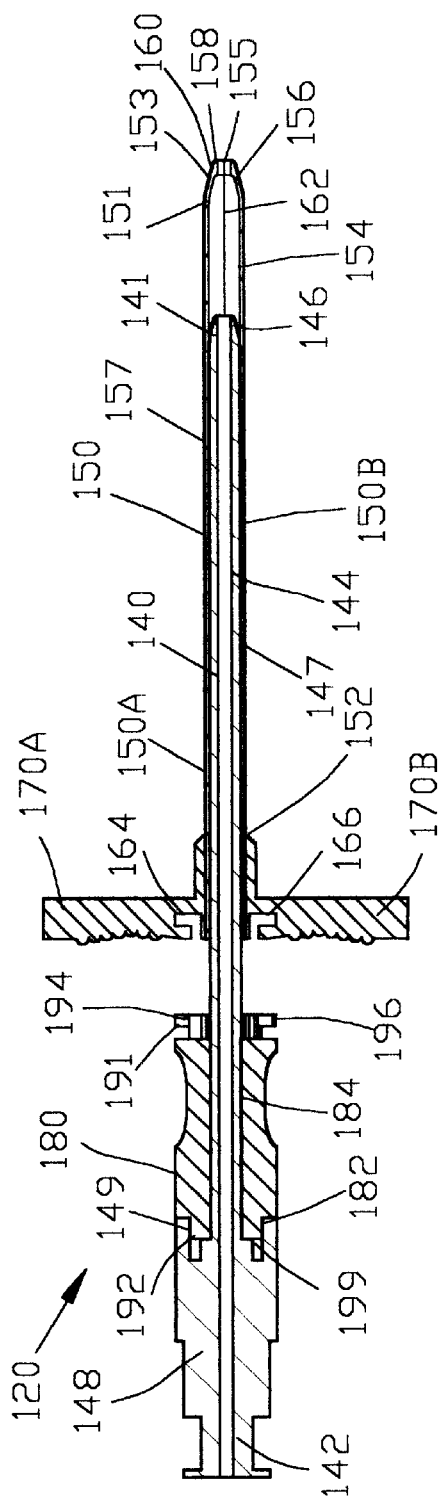
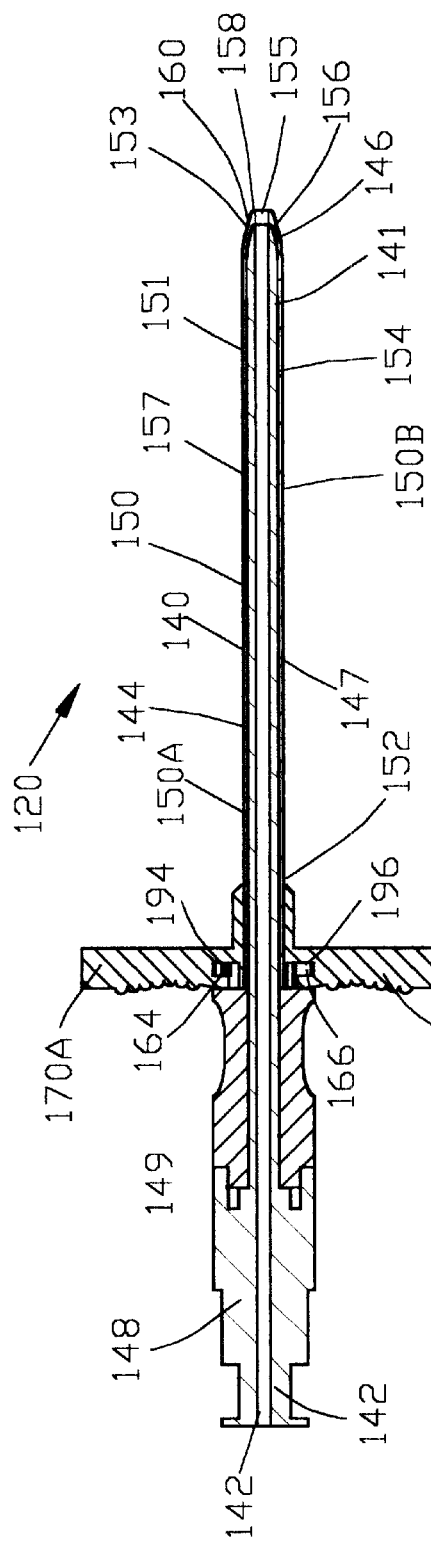

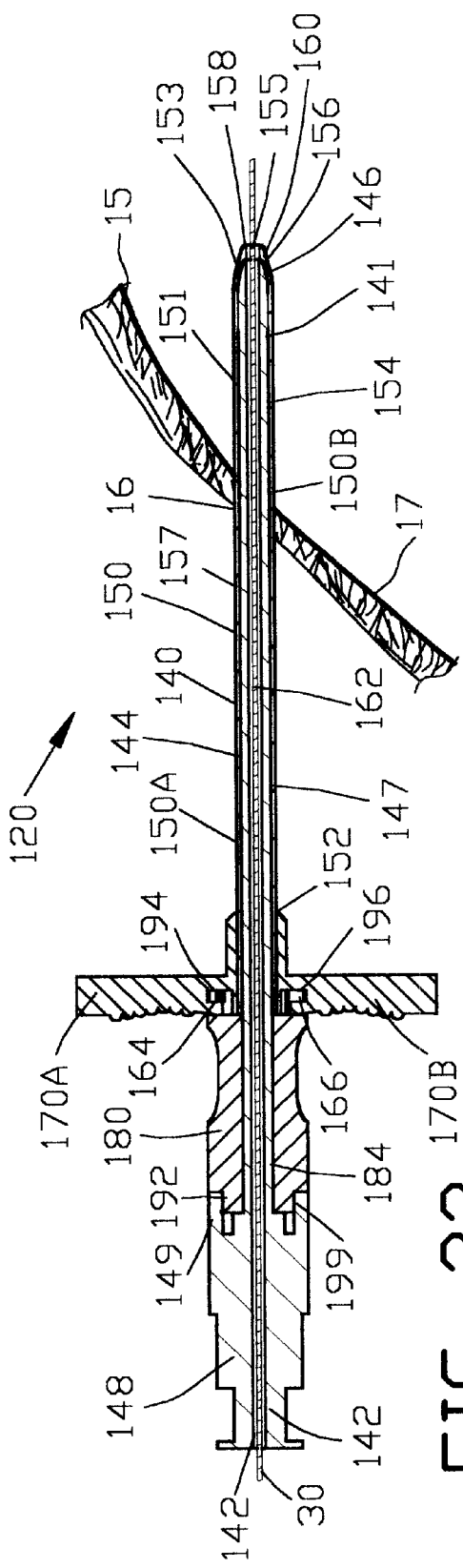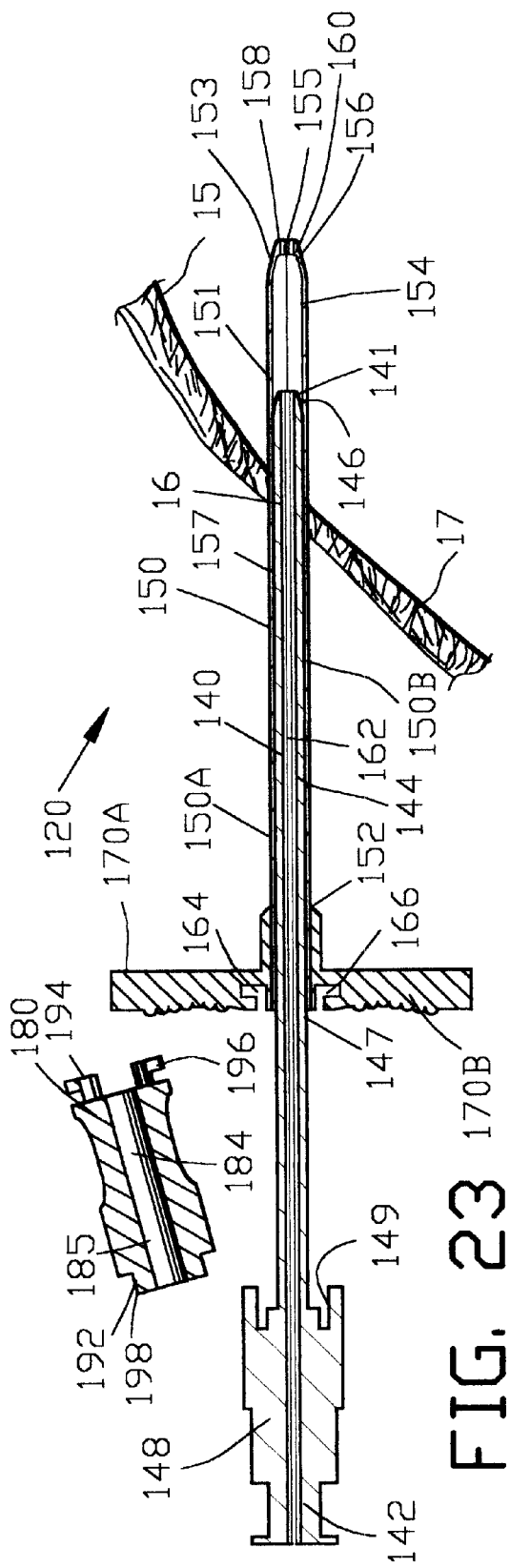

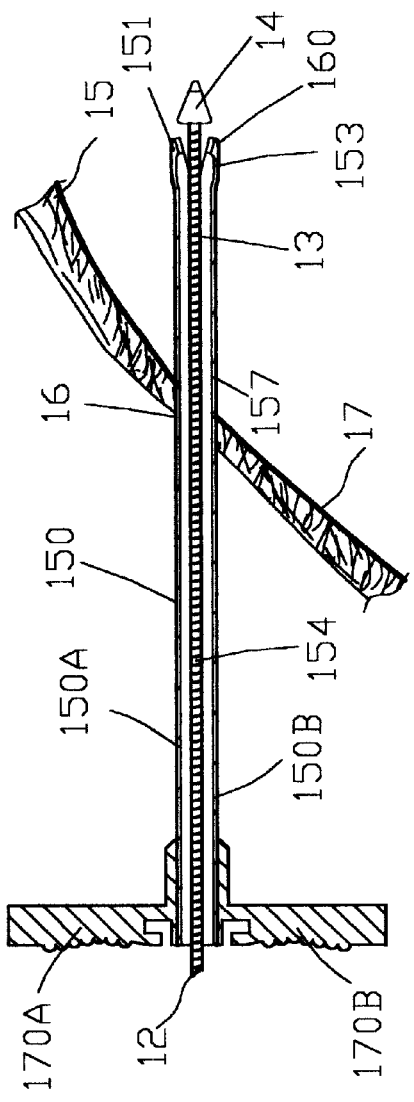
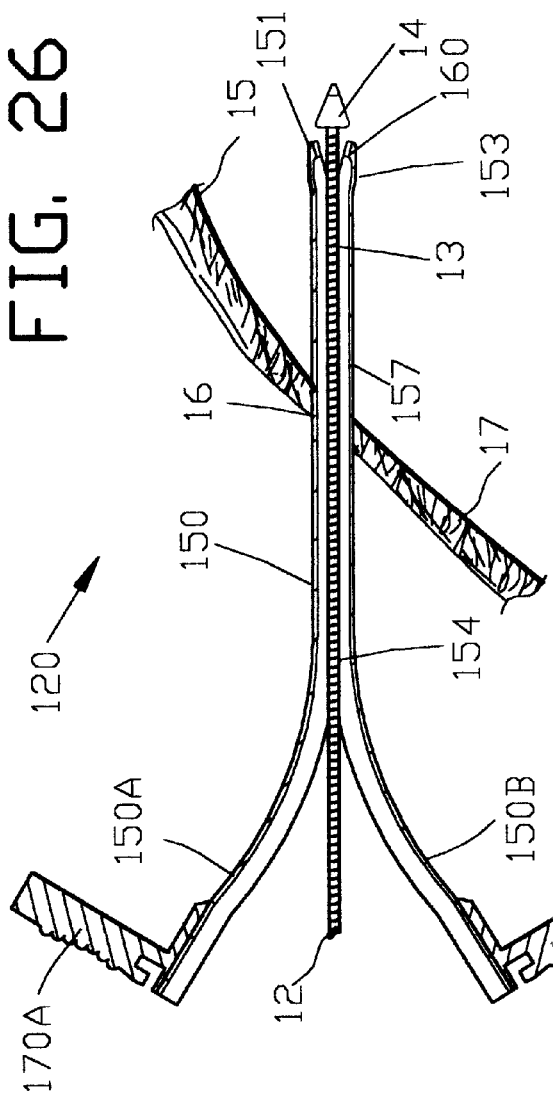
FIG. 26
FIG. 27

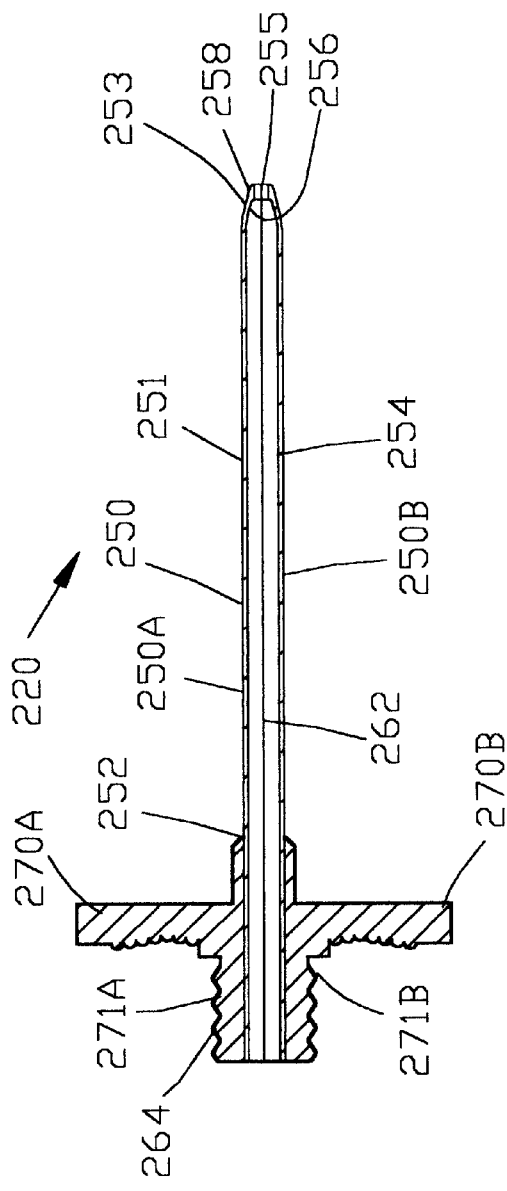
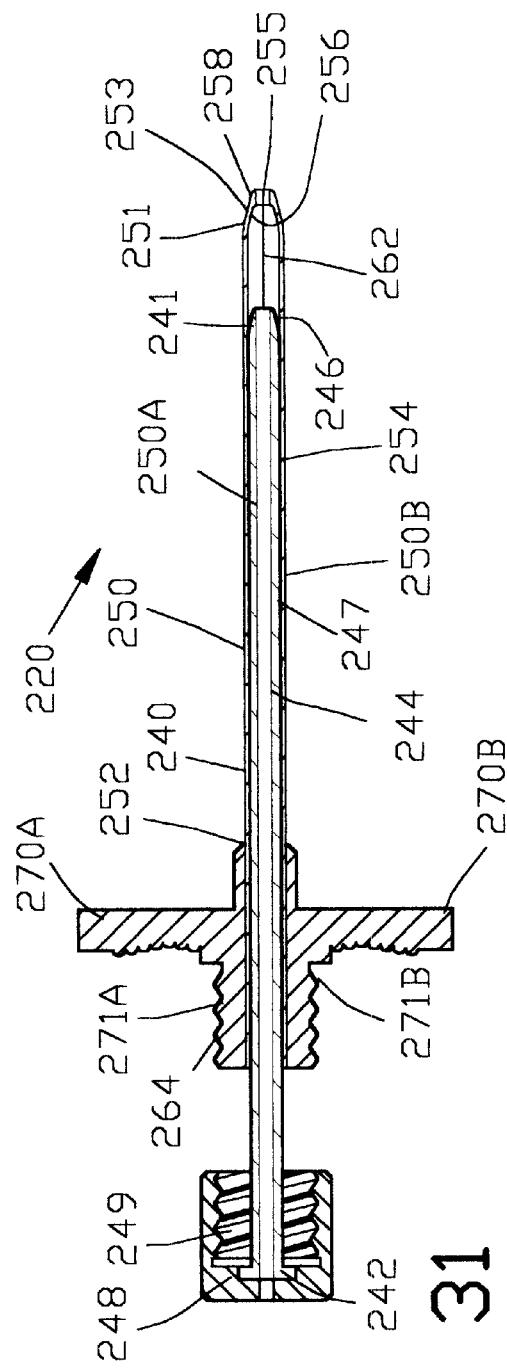
FIG. 30
FIG. 31

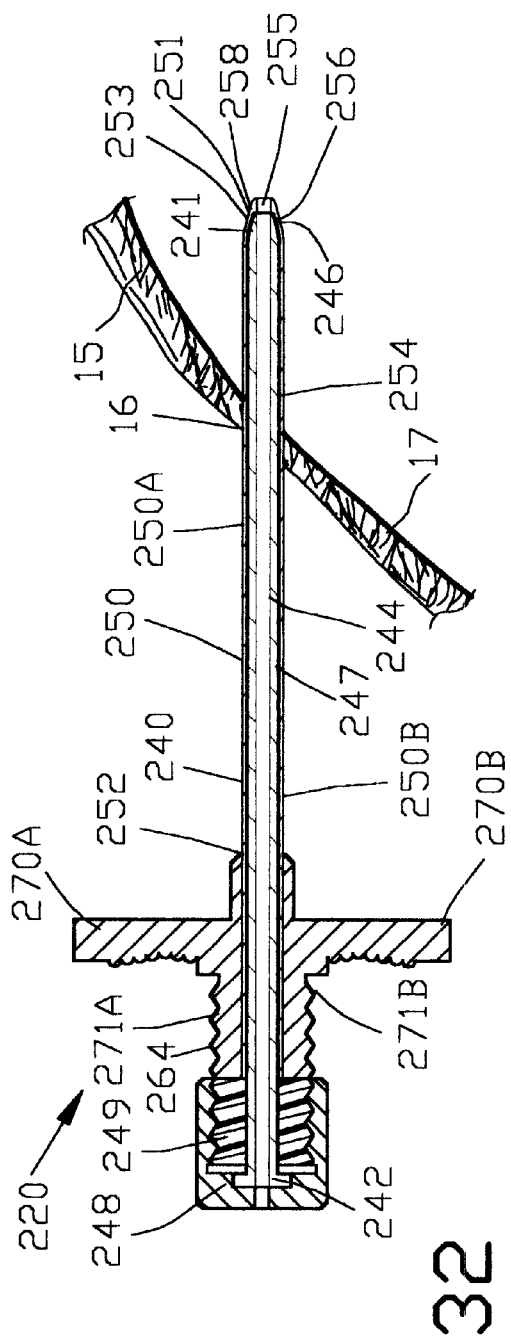
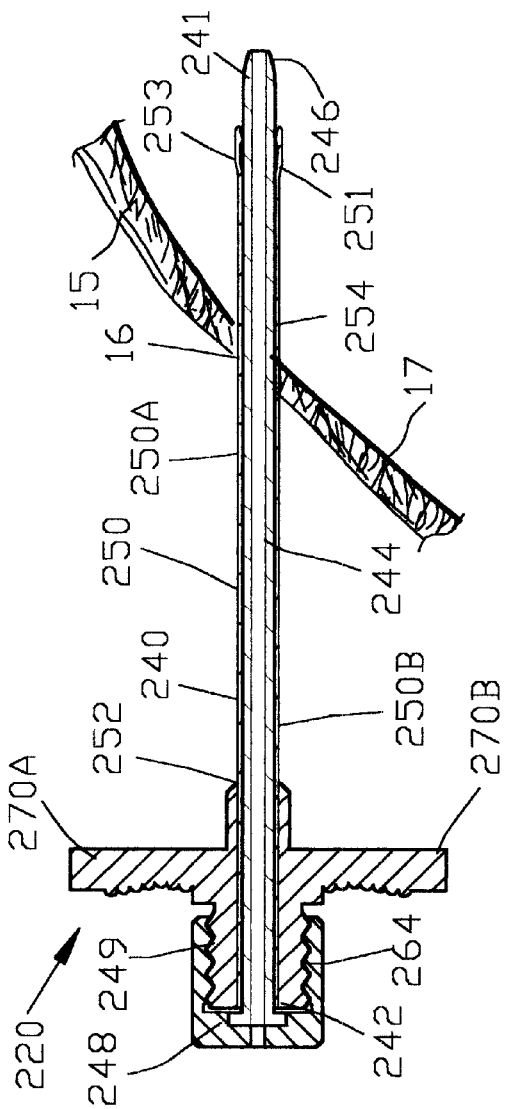
FIG. 32
FIG. 33

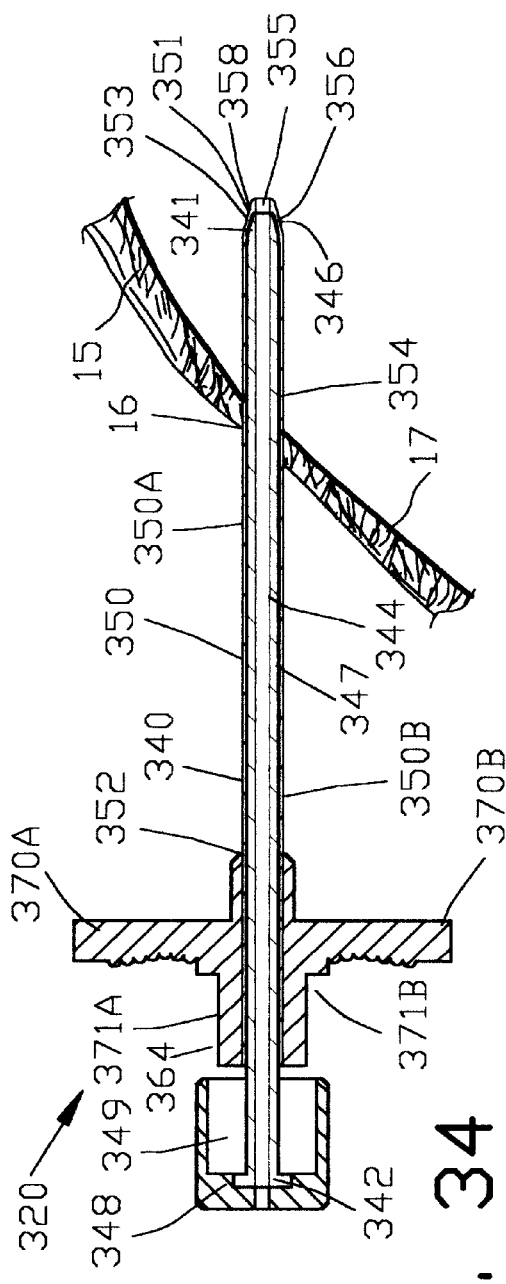
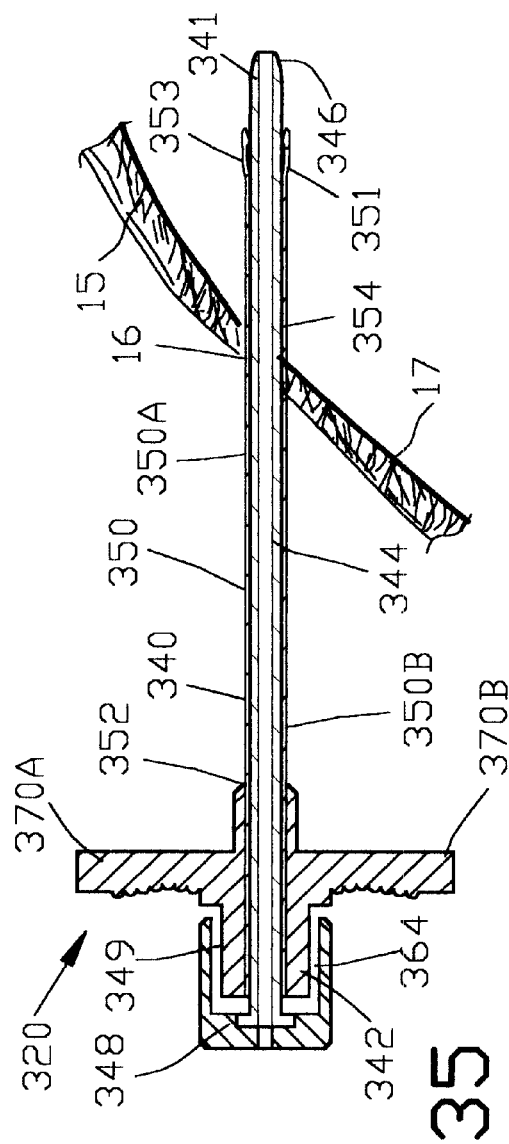
FIG. 34
FIG. 35

APPARATUS FOR INSERTING MEDICAL DEVICE

CROSS-REFERENCE TO RELATED APPLICATIONS

This is a continuation-in-part of U.S. patent application Ser. No. 08/790,708 filed Apr. 21, 1997, now abandoned. All subject matter set forth in application Ser. No. 08/790,708 is hereby incorporated by reference into the present application as if fully set forth herein.

BACKGROUND OF THE INVENTION

1. Field of the Invention

This invention relates to medical devices and more particularly to an improved apparatus and method for inserting a medical device into a patient.

2. Background of the Invention

The prior art has known of various apparatuses and methods for introducing a medical device into a patient. These medical devices include cardiovascular catheters, catheter tubes, pacemaker electrodes or other medical devices that are inserted into a vein or artery of the patient.

One popular method was the Seldinger technique which utilized an apparatus comprising a dilator and a sheath. The dilator was formed from a rigid plastic tubular material terminating in a tapered tip. The sheath was formed from a flexible plastic material with a scored line extending along the length of the sheath. The sheath was carried on the dilator in a sliding relationship.

A puncture was made in the patient with a needle attached to a syringe. A flexible guide wire was passed through the needle into the patient and the needle and syringe were removed from the patient. The dilator and carried sheath was moved along the flexible guide wire into the original incision for opening or dilating the original incision and for positioning the dilator and the carried sheath within the vein or artery of the patient.

After the dilator and carried sheath was positioned in the desired region of the patient, the guide wire and the dilator were removed leaving the sheath positioned within the tissue. An internal bore of the sheath provided a conduit for introducing the medical device into the tissue and for positioning the device thereby. After the medical device was properly positioned within the tissue, the sheath was withdrawn from the tissue.

In many cases, the sheath was removed by peeling away the sheath from the medical device along the scored line extending along the length of the sheath. The device was positioned within the tissue in a simple and efficient manner.

Various forms of the dilator and the sheath apparatuses are available to the prior art. The following U.S. Patents are representative of some of the dilator and the sheath apparatuses for introducing a medical device into a patient.

U.S. Pat. No. 1,064,307 to Fleming discloses a sheath comprising a longitudinally divided body portion, a central fluid passage in the body portion, having a plurality of discharge openings communicating with the central passage and means for interlocking the longitudinally divided body portions. The means comprises dovetailed interlocking portions in the discharge end of the divided body portions, and segmental portions at the receiving end adapted to be inserted into a locking coupling.

U.S. Pat. No. 2,566,499 to Richter discloses an expansible needle assembly comprising an elongated tubular needle having one end substantially pointed and having at its opposite end an enlargement of rectangular cross-sectional shape provided with a counterbore. The needle is longitudinally divided into two substantially identical parts. A U-shaped bracket receives the enlarged portion of the needle means attaching one part of the needle to one leg of the bracket. The other leg of the bracket has a screw threaded aperture therein, a thumbscrew threaded through the aperture, and means rotatably connecting the thumbscrew to the other part of the needle at the end of the thumbscrew adjacent the other needle part.

U.S. Pat. No. 4,772,266 to Groshong discloses a dilator/sheath assembly for unstressed placement of catheter tubes into a body cavity of medical patients, which insure a stable axial relationship between concentrically superimposed sheath and dilator so that use is very facile for the medical attendant and insures a predetermined two-step gentle enlargement of a puncture site to accommodate unstressed placement of a catheter tube into a vein or artery through the puncture site and with minimal trauma to the patient.

U.S. Pat. No. 4,747,833 to Kousai et al. discloses a medical instrument-guiding tube for guiding a catheter or other rod-like medical instrument into a blood vessel. This guiding tube comprises a hollow tube body and at least one linear body integrally joined to the tube body along the longitudinal direction of the tube body. The plastic resin forming the tube body has a poor compatibility with that of linear body. The tube body and the linear body are engaged together through a complementary concave-convex engagement which can be disengaged with a reasonable force.

U.S. Pat. No. 4,840,613 to Balbierz discloses an improvement in a catheter assembly including a cannula, an inserter having a guide channel therethrough in which the cannula slidably fits and a hub structure with the cannula proximal end portion attached to the hub structure. The improvement includes a sheath having a longitudinal slit or weakened portion and being about the cannula between the inserter and the hub structure. A sheath stripping construction carried by the inserter strips the sheath from about the cannula as the cannula slides distally through the guide channel. A first lock member is carried by the inserter and an interlocking second lock member is located about the cannula between the inserter and the hub structure. The cannula is protected from contamination and from kinking and a positive lock serves to prevent its accidental withdrawal. A method of inserting a cannula using such an assembly is likewise set forth.

U.S. Pat. No. 5,098,392 to Fleischhacker et al. discloses a locking dilator and peel away introducer sheath assembly for preventing undesired rearward migration of a dilator within an introducer sheath to insure a proper longitudinal relationship. The dilator has secured to its proximal end a gripping clamp for holding securely the handle of the introducer sheath to accommodate placement of the dilator and introducer sheath into an appropriate location within a patient resulting in minimal tissue damage and trauma.

U.S. Pat. No. 5,154,703 to Bonaldo discloses a medical device which prevents the backflow of fluid therethrough and is particularly useful as a bloodless catheter assembly, that is, prevents the backflow of blood through the catheter by utilization of a self-closing valve carried in a hollow catheter housing to one end of which a catheter is fixed so as to provide a fluid passage through the catheter and catheter housing. The fluid passage in the catheter housing is sealed by a self-sealing valve element extending transversely across the passage upstream from the catheter. A hollow needle is held in the catheter housing downstream of and pointed at the valve element. Attachment of a fluid dispensing medical device to the other catheter housing end forces the valve element downstream onto the needle so as to pierce the valve element and open a fluid passage from the catheter housing upstream of the valve element through the hollow needle to the catheter. Removal of the medical device permits the resiliently biased valve element to move upstream away from the needle, thereby resealing and thus reclosing the fluid passage which extends through the hollow needle.

U.S. Pat. No. 5,125,904 and U.S. Pat. No. 5,312,355 to Lee discloses a splittable hemostatic valve and introducer sheath provided for introductions of leads or catheters through the valve and sheath combination into a vein or artery. Because of the hemostatic valve, this sheath can remain in the vein throughout the operation with the advantage of free lead exchange possibility and easier lead manipulation, especially in dual lead insertions, without bleeding, risk of air embolism or repeated sheath insertion related trauma for lead exchange. A side arm to the hemostatic valve cage provides continuous fluid drip in order to prevent clot formation in the lumen of the sheath. At the point in the operation where the introducer sheath and hemostatic valve must be removed from the lead or catheter, which must remain implanted, means are employed to split or separate the introducer sheath and valve apart so that the sheath and valve are removed from the implanted lead or catheter without the necessity of sliding either the sheath or valve over the free end of the lead or catheter. In this manner, any termination which may be provided on the free end of the lead or catheter, such as a terminal for connection to a pacemaker, will not interfere with the optional use of the introducer sheath and hemostatic valve.

U.S. Pat. No. 5,167,634 to Corrigan, Jr. et al. discloses a peelable sheath including a sheath formed of a flexible tube having a pair of separation lines arranged longitudinally on radially opposite sides of the tube to form a pair of peelable sheath portions, and a hub connector bonded to the proximal end of the sheath. A pair of wings are bonded to the proximal end of the sheath to facilitate separation. The hub connector and sheath are bonded by a web extending axially from a shoulder of the hub connector and including a pair of web tabs arranged on radially opposite sides of the hub connector. The web tabs are bonded to the sheath across respective separation lines, thereby preventing premature separation of the peelable sheath portions. The web also includes a pair of web support struts, arranged on radially opposite sides of the hub and rotated about 90° relative to the web tabs, that are bonded to the respective wings to prevent premature separation of the hub connector from the sheath.

U.S. Pat. No. 5,380,292 to Wilson discloses an adjustable needle mechanism for gastrointestinal use in combination with an endoscope. The needle is received within a catheter or sheath and is movable between a first position in which it projects out of the catheter and a second position in which it is withdrawn into the catheter. A rotatable knob is provided to adjust the extent of projection of the needle when it is in the first position thereby eliminating any necessity to trim the end of the catheter.

U.S. Pat. No. 5,397,311 to Walker et al. discloses an apparatus provided for facilitating substantially bloodless insertion into and withdrawal from a patient's body of a longitudinal member having a proximal end portion and having a distal end portion which is adapted to extend into the patient's body. The apparatus comprises a longitudinally extending sleeve having proximal and distal end portions and defining a lumen extending there along. The longitudinal member is positioned along the lumen. The sleeve has a line extending longitudinally along it which is either split or splittable so that the sleeve can be separated along the line for removal from about the longitudinal member while the distal end portion of the longitudinal member remains extended into the patient. A valve structure serves for preventing blood flow through the lumen. An access is present for allowing substantially bloodless insertion and withdrawal of the longitudinal member through the lumen.

U.S. Pat. No. 5,584,820 to Gurmarnik discloses a set for spinal anesthesia that has a hollow introducer needle, a spinal needle introducible through the introducer needle into subarachnoid space, and a separate elongated hollow fixing element having a first portion which is fixable with the introducer needle, and a second portion surrounding exclusively the spinal needle and fixable with the spinal needle, so that the spinal needle is movable through the means between a plurality of positions and is fixed by the second portion to the fixing element in each of the positions.

U.S. Pat. No. 5,613,953 to Pohndorf discloses a transvenous lead introducer having an integral mechanical valve assembly which includes opposed coacting valve members that are operated by opposed handles. The handles of the valves are joined by rotatably link assemblies and are normally biased in a closed position by integrally formed bias springs.

Although the aforementioned apparatus has provided benefit to the medical community, the use of the combination of dilator and sheath suffered from certain inherent problems. Firstly, the sheath carried by the dilator formed a step or shoulder by the distal sheath end of the sheath at the juncture of the sheath and the dilator. The step or shoulder formed by the distal sheath end of the sheath hindered the insertion of the dilator within the tissue. Secondly, the step or shoulder formed by the distal sheath end of the sheath produced undesirable trauma and damage to the tissue as the dilator was inserted into the patient.

To overcome this difficulty some in the prior art had attempted to taper the distal sheath end of the sheath in order to reduce the shoulder formed thereby and to avoid the aforementioned disadvantages of the prior art. Unfortunately, the extent at which the distal sheath end of the sheath could be tapered was limited since such tapering reduced the mechanical strength of the distal sheath end of the sheath. For many years, this unsolved problem has existed in the medical art.

Therefore it is an object of the present invention to provide an improved apparatus for inserting a medical device into a patient which overcomes the disadvantages of the inherent problems of the prior art.

Another object of this invention is to provide an improved apparatus for inserting a medical device into a patient having a smooth outer surface to eliminate all problems associated with the step or shoulder formed at the juncture of the dilator and the sheath of the prior art devices.

Another object of this invention is to provide an improved apparatus for inserting a medical device into a patient having a smooth outer surface to eliminate the step or shoulder formed at the juncture of the dilator and the sheath of the prior art devices.

Another object of this invention is to provide an improved apparatus for inserting a medical device into a patient wherein a sheath having a smooth outer surface functions to dilate the tissue of the patient.

Another object of this invention is to provide an improved apparatus for inserting a medical device into a patient which provides the same ease and use as found in the prior art devices.

Another object of this invention is to provide an improved apparatus for inserting a medical device into a patient which is substantially the same or a reduced cost from the prior art devices.

Another object of this invention is to provide an improved apparatus for inserting a medical device into a patient which can be sterilized in a same or similar fashion as the prior art.

Another object of this invention is to provide an improved apparatus for inserting a medical device into a patient including a novel device for interlocking the sheath with a hub assembly.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention with in the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved apparatus for inserting a medical device into a patient. The improved apparatus comprises an obturator defining a distal obturator end. A sheath has an internal bore terminating at a distal sheath end. The internal bore of the sheath receives the obturator with the obturator supporting the sheath for enabling the sheath to be inserted within the patient. The obturator is advanced relative to the sheath to fracture the distal sheath end. The obturator is removable from the sheath for enabling the medical device to be inserted through the sheath to enter into the patient. The sheath is removable from the patient while the medical device remains within the patient.

In a more specific embodiment of the invention, the internal bore of the sheath receives the obturator in a sliding engagement with the substantially rigid obturator supporting the substantially flexible sheath for enabling the substantially flexible sheath to be inserted within the patient. The distal sheath end of the sheath has a sheath endwall at least partially enclosing the distal sheath end of the sheath. The distal obturator end of the obturator fractures the sheath endwall upon advancement of the obturator relative to the sheath.

In one embodiment of the invention, the obturator extends between the distal obturator end and a proximal obturator end with the distal obturator end having an external obturator taper. The sheath extends between the distal sheath end and a proximal sheath end. The distal sheath end has an internal sheath taper and an external sheath taper. The internal sheath taper of the distal sheath end conforms to the external obturator taper for supporting the distal sheath end for enabling the external sheath end to be inserted within the patient. The external obturator taper of the obturator fractures the sheath endwall upon advancement of the obturator relative to the sheath.

In another embodiment of the invention, the apparatus includes a hub assembly for attaching the obturator relative to the sheath for enabling the sheath to be inserted within the patient. The hub assembly detaches the obturator relative to the sheath for permitting advancement of the obturator relative to the sheath to fracture the distal sheath end. The hub assembly may include a removable coupling for attaching the obturator relative to the sheath to position the tapered distal obturator end adjacent to the tapered distal sheath end. The removable coupling is removable for permitting limited advancement of the obturator relative to the sheath to fracture the distal sheath end.

In the alternative, the hub assembly includes a threaded member for attaching the obturator relative to the sheath to position the tapered distal obturator end adjacent to the tapered distal sheath end. The threaded member permits limited advancement of the obturator relative to the sheath to fracture the distal sheath end.

The sheath may include a frangible region defined in the sheath for enabling the sheath to be removed from the patient and from the medical device while the medical device remains within the patient. Preferably, the frangible region extends to the external sheath taper for facilitating the fracture of the distal sheath end upon the advancement of the obturator relative to the sheath.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 3 is a view similar to FIG. 2 illustrating a dilator and a sheath moving along the flexible guide wire for dilating the original puncture within the patient;

FIG. 4 is a view similar to FIG. 3 illustrating the removal of the dilator from the patient;

FIG. 10 is an enlarged view of a portion of FIG. 8;

FIG. 10A is an end view of FIG. 10;

FIG. 11 is an enlarged sectional view of a portion of FIG. 9;

FIG. 11A is a sectional view along line 11A—11A in FIG. 11A;

FIG. 12 is a side view of a first embodiment of an improved obturator of the present invention;

FIG. 13 is a sectional view of the improved obturator of FIG. 12;

FIG. 14 is a side view of a first embodiment of an improved sheath of the present invention;

FIG. 14A is a right side view of FIG. 14;

FIG. 15 is a sectional view of the improved sheath of FIG. 14;

FIG. 15A is a left side view of FIG. 15;

FIG. 18 illustrates the coupling of FIGS. 16 and 17 being positioned adjacent to the improved obturator of FIGS. 12 and 13;

FIG. 19 illustrates the connection of the coupling with the improved obturator shown in FIG. 18;

FIG. 20 illustrates the coupling and the improved obturator of FIG. 19 being inserted within the improved sheath of FIGS. 14 and 15;

FIG. 21 illustrates the attachment of the improved obturator and the coupling to the improved sheath;

FIG. 22 illustrates the improved obturator and the coupling and the improved sheath moving along the flexible guide wire for dilating the original puncture;

FIG. 23 illustrates the removal of the flexible guide wire and the removal of the coupling;

FIG. 26 illustrates the introduction of the medical device through the sheath;

FIG. 27 illustrates the peeling away of the sheath from the medical device;

FIG. 30 is a side sectional view of a second embodiment of an improved sheath of the present invention;

FIG. 31 is a side sectional view of the improved obturator of FIG. 29 being inserted within the improved sheath of FIG. 30;

FIG. 32 illustrates the improved obturator and the improved sheath of FIG. 31 dilating the original incision;

FIG. 33 illustrates the advancement of the improved obturator relative to the improved sheath for fracturing the endwall of the improved sheath;

FIG. 34 is a side sectional view of a third embodiment of an improved obturator and an improved sheath dilating the original incision; and FIG. 35 illustrates the advancement of the improved obturator relative to the improved sheath for fracturing the endwall of the improved sheath.

Similar reference characters refer to similar parts throughout the several Figures of the drawings.

DETAILED DISCUSSION

FIGS. 1–7 are various views illustrating the process of inserting a medical device 10 within a patient 15 through the use of an introducer apparatus 20. The process shown in FIGS. 1–7 is well-known in the art and is commonly referred to as the Seldinger procedure. The process of using an introducer apparatus 20 shown in FIGS. 1–7 has been used for introducing various types of medical devices 10 within a patient 15.

Figure 6:
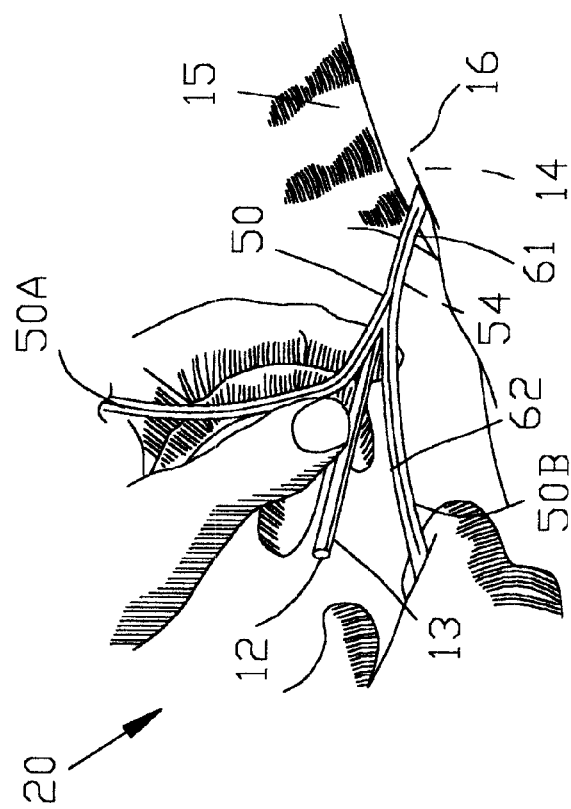
FIG. 6 is a view similar to FIG. 5 illustrating the removal of the sheath from the patient by peeling away of the sheath from the medical device.
Figure 7:
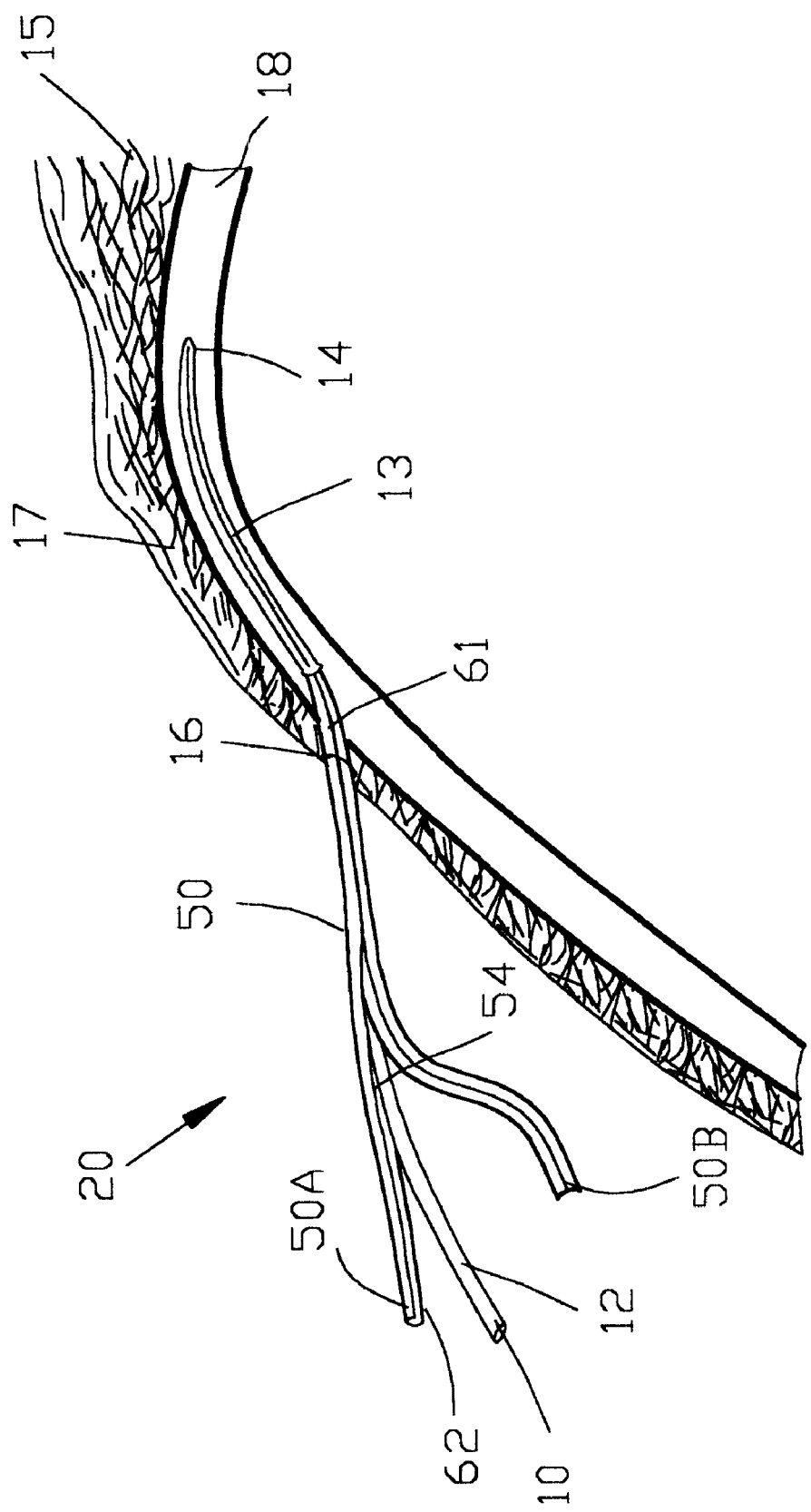
FIG. 7 is an enlarged sectional view of a portion of FIG. 6.
Figure 8:
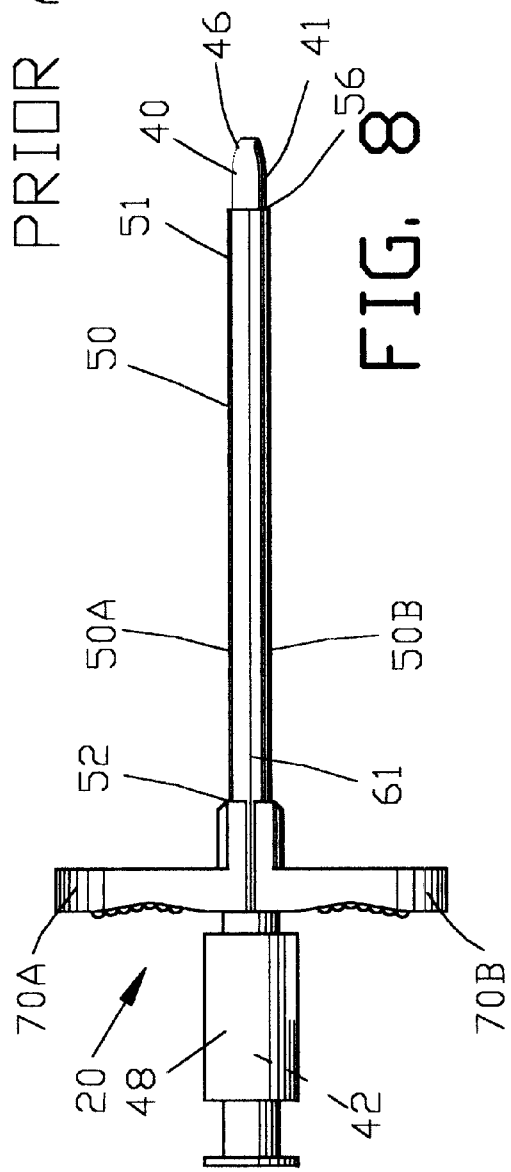
FIG. 8 is a side view of the dilator and sheath of the prior art.
Figure 9:
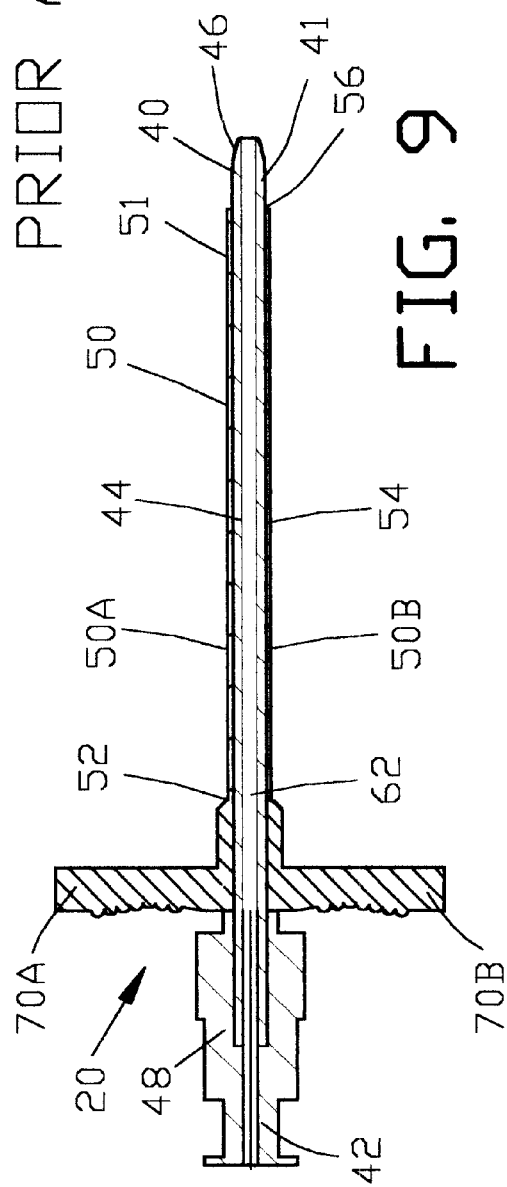
FIG. 9 is a sectional view of the dilator and sheath of FIG. 8.
Figure 17A:
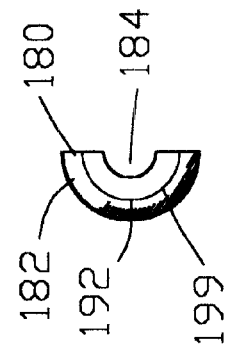
FIG. 17A is a left end view of FIG. 16.

FIG. 7 is an enlarged sectional view of a portion of FIG. 6 illustrating the medical devices 10 as a permanent pacing electrode 12 comprising an insulated flexible electrical connector 13 terminating in an exposed pacing tip 14. The insulated flexible electrical connector 13 and the exposed pacing tip 14 is shown traversing a small incision 16 in the tissue 17 of the patient 15 to extend into the subclavian vein 18 of the patient 15.

Figure 1:
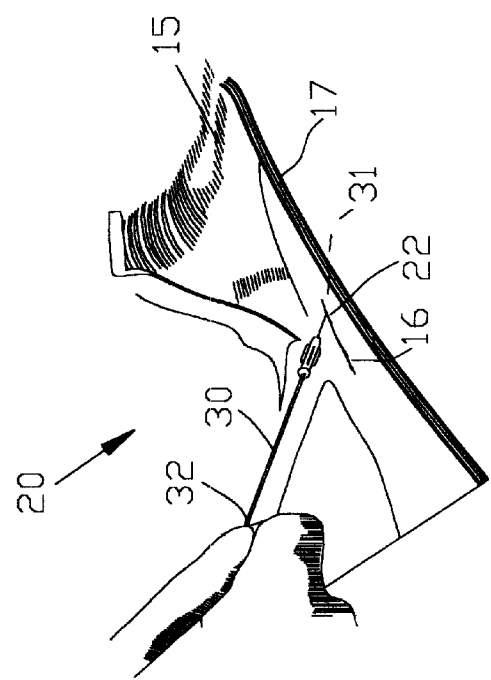
FIG. 1 is an isometric view of a needle attached to a syringe being inserted into a patient.

FIG. 1 illustrates a first step in the process shown in FIGS. 1–7 of inserting a needle 22 attached to a syringe 24 into the patient 15. The needle 22 is aimed toward the desired entrance within the patient 15 such as the subclavian vein 18 as shown in FIG. 7. When the needle 22 is properly positioned within the vein 18, the venous blood is aspirated and the syringe 24 is removed from the needle 22.

Figure 2:
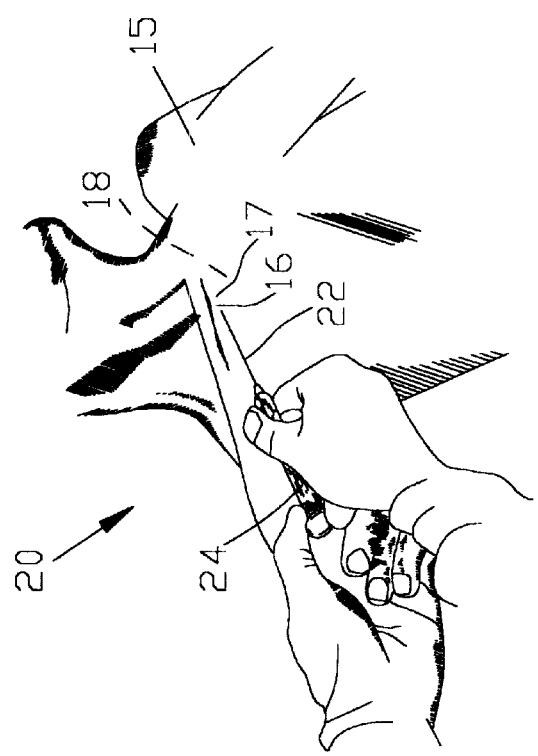
FIG. 2 is an enlarged view of FIG. 1 illustrating the removal of the syringe and the insertion of a flexible guide wire through the needle and into the patient.

FIG. 2 illustrates a second step in the process shown in FIGS. 1–7 of inserting a flexible guide wire 30 through the needle 22 after the needle is properly positioned within the vein 18. The flexible guide wire 30 extends between a first and a second end 31 and 32. The flexible guide wire 30 is selected to be readily threaded through the needle 22. The first end 31 of the flexible guide wire 30 is guided through the needle 22 into the vein 18 until the first end 31 of the flexible guide wire 30 is properly positioned within the vein of the patient 15. When the flexible guide wire 30 is properly positioned within the vein 18, the needle 22 is removed from the patient 15 leaving the flexible guide wire 30 properly positioned within the vein 18 of the patient 15.

FIG. 3 illustrates a third step in the process shown in FIGS. 1–7 of inserting a dilator 40 carrying a sheath 50 into the vein 18 of the patient 15. The dilator 40 and the sheath 50 are guided into the vein 18 of the patient 15 by the flexible guide wire 30. In some procedures, the incision 16 is enlarged in the tissue 17 of the patient 15 prior to the insertion of the dilator 40 and the sheath 50.

FIGS. 8–11 illustrate various views of the dilator 40 and the sheath 50 known to the prior art. The dilator 40 extends between a distal dilator end 41 and proximal dilator end 42 with an internal passage 44 extending therebetween. The distal dilator end 41 of the dilator 40 has a taper 46 for facilitating the insertion into and expansion of the small incision 16 within the tissue 17 of the patient 15. The internal passage 44 of the dilator 40 is adapted to receive the flexible guide wire 30. The proximal dilator end 42 of the dilator 40 supports a dilator hub 48.

The sheath 50 has a distal sheath end 51 and a proximal sheath end 52 with an internal bore 54 extending therebetween. The internal bore 54 of the sheath 50 is adapted to slidingly receive the dilator 40. The distal sheath end 51 of the sheath 50 is spaced from the taper 46 of the distal dilator end 41 of the dilator 40 thereby creating a shoulder 56 at the distal sheath end 51 of the sheath 50.

The sheath 50 is fabricated from a thin wall polymeric material to minimize the size of the shoulder 56 at the distal sheath end 51 of the sheath 50. The thin polymeric wall of the sheath 50 requires the mechanical strength of the dilator 40 in order to carry the sheath 50 through the insertion and expansion of the small incision 16 within the tissue 17 of the patient 15.

The sheath 50 is provided with weakening or score lines 61 and 62 extending along the longitudinal length of the sheath 50 between the distal sheath end 51 and the proximal sheath end 52. The weakening or score lines 61 and 62 divide the sheath 50 into a first sheath portion 50A and a second sheath portion 50B extending along the longitudinal length of the sheath 50 between the distal sheath end 51 and the proximal sheath end 52. The sheath 50 may be provided with a first and a second handle 70A and 70B respectively secured to first and second sheath portions 50A and 50B. The first and second handles 70A and 70B facilitate the separation or peeling of the sheath 50 into the first and second sheath portions 50A and 50B along the weakening or score lines 61 and 62 as will be described greater detail hereinafter.

FIG. 3 illustrates the internal passage 44 of the dilator 40 being threaded on the second end 32 of the guide wire 30. The internal passage 44 of the dilator 40 receives the flexible guide wire 30 and directs the dilator 40 and the sheath 50 along the flexible guide wire 30. The taper 46 of the distal dilator end 41 of the dilator 40 facilitates the insertion into small incision 16 and expands the small incision 16 within the tissue 17 of the patient 15. The dilator 40 and the sheath 50 are guided by the flexible guide wire 30 into the vein 18 until the distal sheath end 51 of the sheath 50 is properly positioned within the vein of the patient 15.

FIG. 4 illustrates a fourth step in the process shown in FIGS. 1–7 of removing the dilator 40 from the patient 15 and the sheath 50. The sheath 50 remains within the patient with the distal sheath end 51 being properly positioned within the vein 18.

Figure 5:
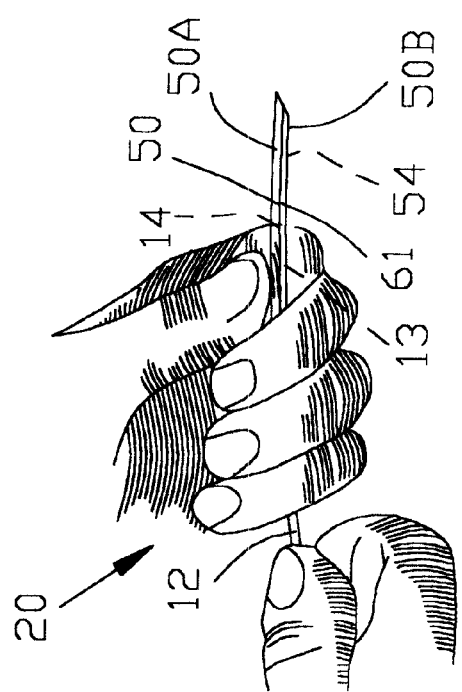
FIG. 5 is a view similar to FIG. 4 illustrating the introduction of a medical device through an internal bore of the sheath into the patient.

FIG. 5 illustrates a fifth step in the process shown in FIGS. 1–7 of introducing the medical device 10 through the internal bore 54 of the sheath 50 and into the vein 18 of the patient 15. In this example, the exposed pacing tip 14 of the pacing electrode 12 is inserted into the proximal sheath end 52 and moved along the internal bore 54 of the sheath 50 until the exposed pacing tip 14 is properly positioned within the patient 15.

FIG. 6 illustrates a sixth step in the process shown in FIGS. 1–7 of removing the sheath 50 from the medical device 10 and from the patient 15. The sheath 50 is removed by separating the handles 70A and 70B (shown in FIGS. 3–4 and 8–9) to separate the sheath 50 into the first and second sheath portions 50A and 50B as shown in FIGS. 6 and 7. The sheath 50 is simultaneously separated into the first and second sheath portions 50A and 50B and withdrawn from the patient 15 leaving the medical device 10 within the patient 15.

FIGS. 12–17 illustrate various views of components comprising an improved introducer apparatus 120 of the present invention for introducing the medical appliance 10 into the patient 15 in a manner similar to the process shown in FIGS. 1–7. The operation of the improved introducer apparatus 120 of the present invention will be described with reference to the introduction of the permanent pacing electrode 12 into the subclavian vein 18 of the patient 15. However, it should be understood that the improved introducer apparatus 120 of the present invention may be used for introducing many types of medical devices 10 within the patient 15 as should be apparent to those skilled in the art.

FIGS. 12 and 13 are side elevational and side sectional views of an improved obturator 140 comprising a portion of the improved introducer apparatus 120 of the present invention. The obturator 140 extends between a distal obturator end 141 and proximal obturator end 142 with an internal passage 144 extending therebetween. The distal obturator end 141 of the obturator 140 has an external obturator taper 146 terminating from an external surface 147. The internal passage 144 of the obturator 140 is adapted to receive the flexible guide wire 30 shown in FIGS. 2–4. The proximal obturator end 142 of the obturator 140 supports an obturator hub 148. The hub 148 is provided with hub threads 149. The structure and function of the obturator hub 148 and the hub threads 149 will be described in greater detail hereinafter. Preferably, the obturator 140 is substantially rigid and fabricated from a polymeric material such as high density polyethylene or the like.

FIGS. 14 and 15 are side elevational and side sectional views of an improved sheath 150 comprising a portion of the improved introducer apparatus 120 of the present invention. FIGS. 14A and 15A are views of FIGS. 14 and 15 respectively. The improved sheath 150 has a distal sheath end 151 and a proximal sheath end 152. The distal sheath end 151 of the sheath 150 has a sheath endwall 153 at least partially enclosing the distal sheath end 151 of the sheath 150. The improved sheath 150 has an internal bore 154 extending from the proximal sheath end 152 and terminating at the sheath endwall 153 of the distal sheath end 151.

A sheath passage 155 extends through the sheath endwall 153 of the distal sheath end 151. The cross-section of the sheath passage 155 is smaller than the cross-section of the internal bore 154 of the sheath 150. The internal bore 154 of the sheath 150 is adapted to slidingly receive the obturator 140 whereas the sheath passage 155 is adapted to receive the flexible guide wire 30 shown in FIGS. 2–4.

The sheath endwall 153 of the distal sheath end 151 of the improved sheath 150 defines an external sheath taper 156 extending from an external surface 157 of the improved sheath 150. The sheath endwall 153 defines an internal sheath taper 158. The external sheath taper 158 is tapered at an angle for enabling the external sheath taper 158 to be inserted within the patient 15. The internal sheath taper 156 of the distal sheath end 151 is tapered to conforms to the external obturator taper 146 of the improved obturator 140.

The improved sheath 150 is provided with a frangible region 160 defined in the improved sheath 150 for enabling the improved sheath 150 to be removed from the patient 15 and from the medical device 10 while the medical device 10 remains within the patient 15. The frangible region 160 may include the frangible line 161 extending along the improved sheath 150 for enabling the sheath 150 to be removed from the patient 15 and from the medical device 10. Preferably, frangible region 160 includes weakening or score lines 161 and 162 extending along the longitudinal length of the improved sheath 150 between the distal sheath end 151 and the proximal sheath end 152. The weakening or score lines 161 and 162 divide the improved sheath 150 into a first sheath portion 150A and a second sheath portion 150B.

As best shown in FIG. 14A, the frangible region 160 extends into the sheath endwall 153 of the improved sheath 150. Preferably, the weakening or score lines 161 and 162 extend into the sheath endwall 153 to be disposed on the external sheath taper 158. As will be described in greater detail hereinafter, the frangible region 160 extending into the sheath endwall 153 of the improved sheath 150 facilitates the fracturing of the distal sheath end 151 upon the advancement of the improved obturator 140 relative to the improved sheath 150.

The improved sheath 150 may be provided with a first and a second handle 170A and 170B respectively secured to first and second sheath portions 150A and 150B. The first and second handles 170A and 170B facilitate the separation or peeling of the sheath 150 into the first and second sheath portions 150A and 150B along the weakening or score lines 161 and 162 as heretofore described. The first and second handles 170A and 170B define recesses 164 and 166.

Preferably, the improved sheath 150 is fabricated from a thin wall polymeric material to make the improved sheath 150 substantially flexible. The thin polymeric wall of the improved sheath 150 requires the mechanical strength of the improved obturator 140 in order to enable the improved sheath 150 to be inserted into and to expand the small incision 16 within the tissue 17 of the patient 15 as will be described in greater detail hereinafter.

The improved introducer apparatus 120 of the present invention may utilizes an optional coupling for securing the improved sheath 150 relative to the improved obturator 140 for enabling the insertion of the improved sheath 150 into the patient 15. The coupling may take many forms and only a few examples of a suitable coupling are set forth herein. It should be appreciated by those skilled in the art that the specific embodiments of the coupling set forth herein may be readily utilized for designing other coupling. It should be appreciated further by those skilled in the art that the coupling is a desirable but an optional addition to the present invention.

FIGS. 16, 16A, 17 and 17A are various views of one example of an optional coupling 180 for use with the improved introducer apparatus 120 of the present invention. The coupling 180 secured the improved obturator 140 and the improved sheath 150 of the present invention. The coupling 180 extends between a first end 181 and a second end 182 with an internal passage 184 extending therebetween. The internal passage 184 is adapted to receive the external surface 147 of the improved obturator 140. The passage 184 includes an aperture 185 for enabling the coupling 180 to be positioned upon and removed from the improved obturator 140 without moving the coupling 180 over the distal obturator end 141 of the improved obturator 140.

The first end 181 of the coupling 180 includes a sheath connector 191 whereas the second end 182 of the coupling 180 includes an obturator connector 192. The sheath connector 191 is shown as a tabs 194 and 196. The obturator connector 192 shown as external threads 199. Preferably, the coupling 180 is substantially rigid and fabricated from a polymeric material such as high density polyethylene or the like.

Figure 16A:
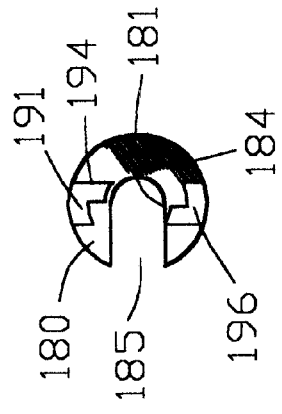
FIG. 16A is a right end view of FIG. 16.
Figure 16:
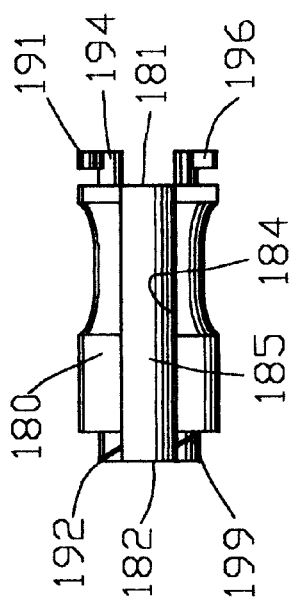
FIG. 16 is an enlarged view of a first embodiment of a coupling for use with the first embodiment of the improved obturator and the improved sheath of the present invention.
Figure 17:
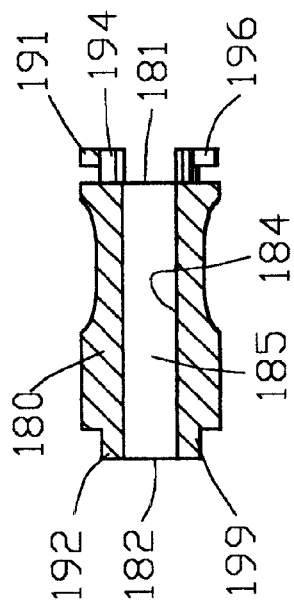
FIG. 17 is a sectional view of FIG. 16.

FIG. 18 is a side sectional view illustrating the positioning of the coupling 180 of FIGS. 16–17 adjacent to the improved obturator 140 of FIGS. 12 and 13. The coupling 180 is inserted onto the improved obturator 140 through the aperture 185.

FIG. 19 is a side sectional view illustrating the connection of the coupling 180 with the improved obturator 140 shown in FIG. 18. The coupling 180 is positioned with the internal passage 184 of the coupling 180 receiving the external surface 147 of the improved obturator 140. The improved obturator 140 is secured to the coupling 180 through the hub threads 149 of the hub 148 engaging with the external threads 199 of the coupling 180. Relative rotation between improved obturator 140 and the coupling 180 results in a threaded engagement between the hub threads 149 and the external threads 199.

FIG. 20 is a side sectional view illustrating the improved obturator 140 of FIG. 18 being inserted within the improved sheath 150 of FIGS. 14 and 15. Preferably, the internal bore 154 of the improved sheath 150 receives the improved obturator 140 in a close sliding engagement. The external surface 147 of the substantially rigid improved obturator 140 supports the internal bore 154 of the substantially flexible improved sheath 150 by virtue of the close sliding engagement therebetween.

FIG. 21 is a side sectional view illustrating the attachment of the improved obturator 140 and the coupling 180 to the improved sheath 150. The improved obturator 140 and the coupling 180 are attached to the improved sheath 150 by the sheath connector 191 engaging the first and second handles 170A and 170B. The tabs 194 and 196 of the sheath connector 191 engage with the recesses 164 and 166 defined within the first and second handles 170A and 170B to attach the improved obturator 140 and the coupling 180 to the improved sheath 150. Relative rotation between improved sheath 150 and the coupling 180 results in an engagement between the tabs 194 and 196 and the recesses 164 and 166.

The coupling 180 attaches the improved obturator 140 relative to the improved sheath 150 to position the tapered distal obturator end 141 adjacent to the tapered distal sheath end 151. The external obturator taper 146 of the obturator distal end 141 of the improved obturator 140 conforms to the internal sheath taper 156 of the distal sheath end 151 of the improved sheath 150. The external obturator taper 146 of the obturator distal end 141 supports the internal sheath taper 156 of the distal sheath end 151 for enabling the external sheath taper 158 to be inserted within the patient 15. The substantially rigid external obturator taper 146 of the improved obturator 140 supports the substantially flexible internal sheath taper 156 of the improved sheath 150 by virtue of the conforming engagement therebetween.

FIG. 22 is a side sectional view illustrating the improved obturator 140, the coupling 180 and the improved sheath 150 moving along the flexible guide wire 30 for dilating the incision 16. The sheath passage 154 of the improved sheath 150 and the internal passage 144 of the improved obturator 140 are threaded on the second end 32 of the guide wire 30. The improved obturator 140, the coupling 180 and the improved sheath 150 move along the flexible guide wire 30. The external sheath taper 148 at the distal sheath end 151 of the improved sheath 150 facilitates the insertion into small incision 16 and expands the small incision 16 within the tissue 17 of the patient 15. The improved obturator 140, the coupling 180 and the improved sheath 150 are guided into the vein 18 of the patient 15 by the flexible guide wire 30.

The prior art apparatus 20 shown in FIGS. 8–11 utilized the dilator 40 to accomplish the insertion into the tissue and the expansion of the tissue 17 of the patient 15. In contrast to the prior art introducer apparatus 20 shown in FIGS. 8–11, the improved introducer apparatus 120 of the present invention utilizes the improved sheath 150 to accomplish the insertion into the tissue and the expansion of the tissue 17 of the patient 15.

The improved introducer apparatus 120 of the present invention eliminates the undesired step or shoulder 56 present in the prior art apparatus 20 shown in FIGS. 8–11. The elimination of the step or shoulder 56 facilitates the insertion within the tissue 17. Furthermore, the elimination of the step or shoulder 56 reduces the trauma and damage to the tissue 17 during the insertion into the patient 15.

FIG. 23 is a side sectional view illustrating the removal of the flexible guide wire 30 and the removal of the coupling 180. Relative rotation between improved obturator 140 and the coupling 180 results in a threaded disengagement between the hub threads 149 and the external threads 199. Relative rotation between improved sheath 150 and the coupling 180 results in a disengagement between the tabs 194 and 196 and the recesses 164 and 166. The removal of the coupling 180 permits only a limited advancement of the improved obturator 140 relative to the improved sheath 150 to fracture the distal sheath end 151 upon the limited advancement of the improved obturator 140 relative to the improved sheath 150.

Figure 24:
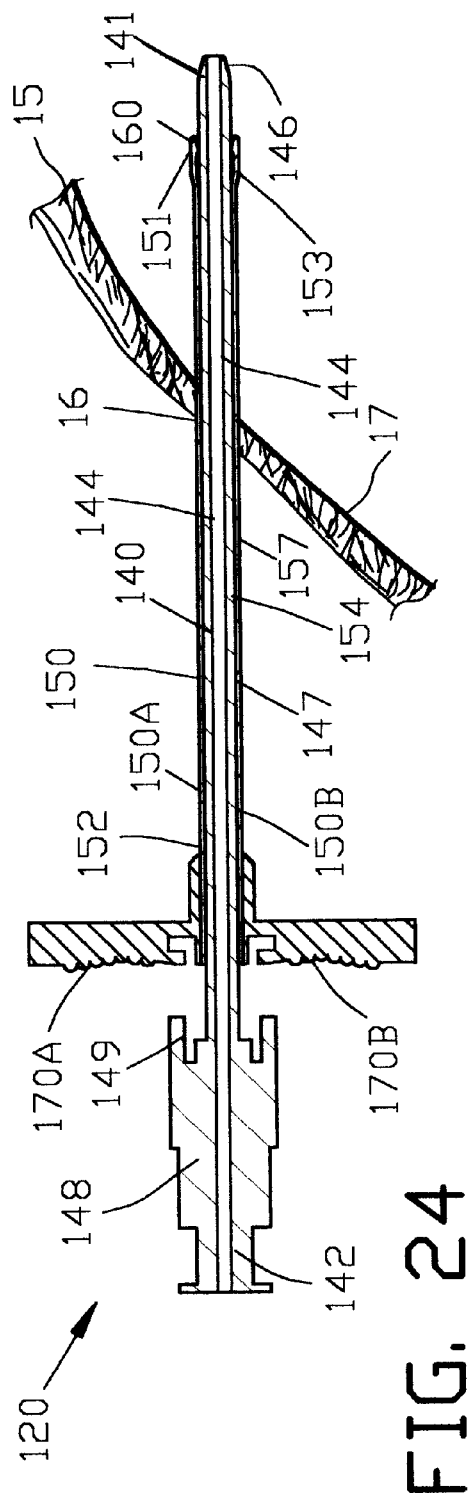
FIG. 24 illustrates the advancement of the improved obturator relative to the improved sheath for fracturing the endwall of the improved sheath.

FIG. 24 is a side sectional view illustrating the advancement of the improved obturator 140 relative to the improved sheath 150 for fracturing the endwall 153 of the improved sheath 150. The external obturator taper 146 of the improved obturator 140 fractures the sheath endwall 153 upon advancement of the improved obturator 140 relative to the improved sheath 150. The advancement of the improved obturator 140 relative to the improved sheath 150 may be accomplished by an operator applying a force between the hub 148 and the first handle and second handle 170A and 170B. The weakening or score lines 161 and 162 extend into the sheath endwall 153 of the improved sheath 150 for facilitating the fracturing of the distal sheath end 151 upon the advancement of the improved obturator 140 relative to the improved sheath 150.

The removal of the coupling 180 permits only a limited advancement of the improved obturator 140 relative to the improved sheath 150. The limiting of the advancement of the improved obturator 140 reduces the possibility of injury to the patient 15 due to excessive movement of the improved obturator 140 upon the fracturing of the sheath endwall 153 of the improved sheath 150.

Figure 25:
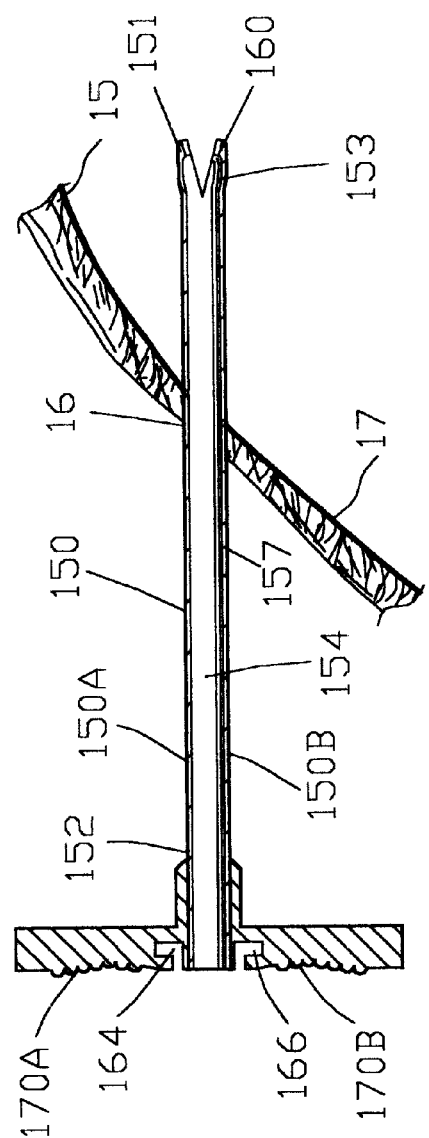
FIG. 25 illustrates the removal of the improved obturator from the improved sheath.

FIG. 25 is a side sectional view illustrating the removal of the improved obturator 140 from the improved sheath 150. The improved obturator 140 is removed from the improved sheath 150 leaving the distal sheath end 151 of the improved sheath 150 property positioned within the patient 15.

The fracturing of the sheath endwall 153 opens the sheath passage 155 to have a cross-section commensurate with the cross-section of the internal bore 154 of the improved sheath 150. The expanded sheath passage 155 enables the medical device 10 to be introduced into the patient 15.

FIG. 26 is a side sectional view illustrating the introduction of the medical device 10 through the improved sheath 150. In this example, the exposed pacing tip 14 of the pacing electrode 12 is inserted into the proximal sheath end 152 and moved along the internal bore 154 of the improved sheath 150 until the exposed pacing tip 14 is properly positioned within the patient 15.

Figure 28:
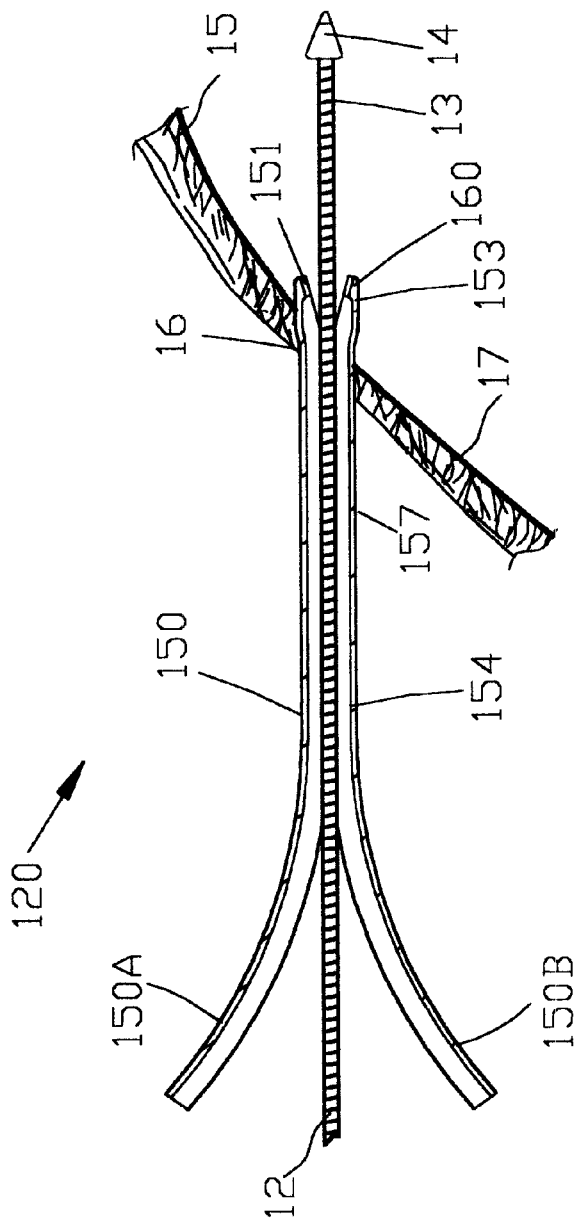
FIG. 28 is an enlarged view of a portion of FIG. 27.

FIGS. 27 and 28 are side sectional views illustrating the peeling away of the improved sheath 150 from the medical device 10. The improved sheath 150 is removed by separating the handles 170A and 170B to separate the improved sheath 150 into the first and second sheath portions 150A and 150B. The improved sheath 150 is simultaneously separated into the first and second sheath portions 150A and 150B and withdrawn from the patient 15 leaving the medical device 10 within the patient 15.

The medical device 10 has been introduced within the patient 15 with reduced trauma and damage to the tissue 17. The reduction in the trauma and damage is due to the elimination of the undesired step or shoulder 56 present in the prior art apparatus 20 shown in FIGS. 8–11.

FIGS. 29–33 illustrate various views of components comprising a second embodiment of an improved introducer apparatus 220 of the present invention for introducing the medical appliance 10 into the patient 15 in a manner similar to. FIGS. 12–29.

Figure 29:
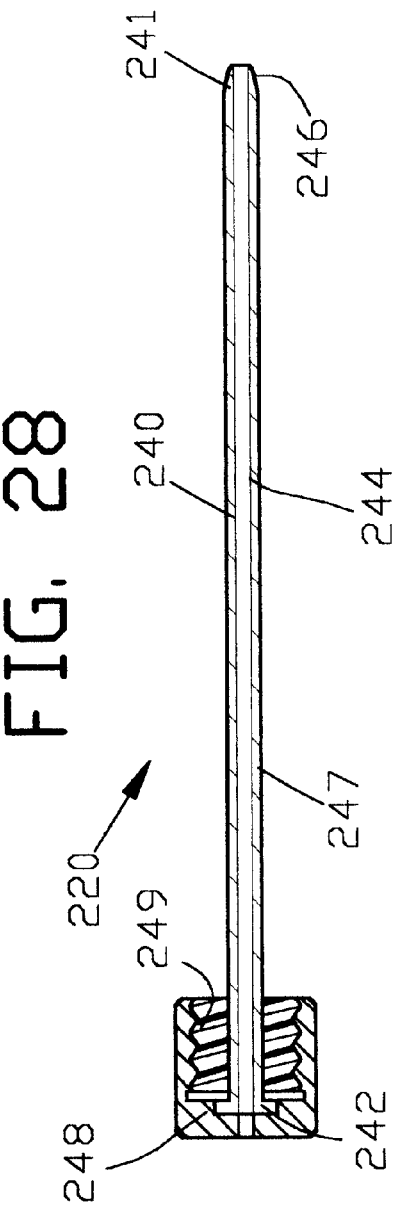
FIG. 29 is a side sectional view of a second embodiment of an improved obturator of the present invention.

FIG. 29 is a side sectional view of a second embodiment of an improved obturator 240 comprising a portion of a second embodiment of the improved introducer apparatus 220 of the present invention. The improved obturator 240 is similar to the improved obturator 140. The obturator 240 extends between a distal obturator end 241 and proximal obturator end 242 with an internal passage 244 extending therebetween. The distal obturator end 241 of the obturator 240 has an external obturator taper 246 terminating from an external surface 247. The internal passage 244 of the obturator 240 is adapted to receive the flexible guide wire 30 shown in FIGS. 2–4. The proximal obturator end 242 of the obturator 240 supports an obturator hub 248. The hub 248 is provided with hub threads 249.

FIG. 30 is a side sectional view of the second embodiment of an improved sheath 250 comprising a portion of the improved introducer apparatus 220 of the present invention. The sheath 250 is similar to the sheath 150. The improved sheath 250 has a distal sheath end 251 and a proximal sheath end 252. The distal sheath end 251 of the sheath 250 has a sheath endwall 253 at least partially enclosing the distal sheath end 251 of the sheath 250. The improved sheath 250 has an internal bore 254 extending from the proximal sheath end 252 and terminating at the sheath endwall 253. A sheath passage 255 extends through the sheath endwall 253 of the distal sheath end 251. The cross-section of the sheath passage 255 is smaller than the cross-section of the internal bore 254 of the sheath 250. The internal bore 254 of the sheath 250 is adapted to slidingly receive an improved obturator 240 whereas the sheath passage 255 is adapted to receive the flexible guide wire 30 shown in FIGS. 2–4.

The sheath endwall 253 of the distal sheath end 251 of the improved sheath 250 defines an external sheath taper 256 extending from an external surface 257 of the improved sheath 250. The sheath endwall 253 defines an internal sheath taper 258. The external sheath taper 258 is tapered at an angle for enabling the external sheath taper 258 to be inserted within the patient 15. The internal sheath taper 256 of the distal sheath end 251 is tapered to conform to the external obturator taper 246 of the improved obturator 240.

The improved sheath 250 is provided with a frangible region 260 including weakening or score lines 261 and 262 as set forth above with reference to the weakening or score lines 161 and 162. The improved sheath 250 is provided with a first and a second handle 270A and 270B respectively secured to first and second sheath portions 250A and 250B.

The improved introducer apparatus 220 of the present invention utilizes a coupling for securing the improved sheath 250 relative to the improved obturator 240 for enabling the insertion of the improved sheath 250 into the patient 15. In this embodiment, the coupling includes threads 264 defined on a first and a second boss portion 271A and 272B extending from the first and second handles 270A and 270B.

FIG. 31 is a side sectional view illustrating the improved obturator 240 being inserted within the improved sheath 250 of FIG. 30. Preferably, the internal bore 254 of the improved sheath 250 receives the improved obturator 240 in a close sliding engagement. The improved obturator 240 is inserted within the improved sheath 250 until the hub 248 engages the first and second boss portion 271A and 272B. When the hub 248 engages the first and second boss portion 271A and 272B, the tapered distal obturator end 241 supports the tapered distal sheath end 151 for enabling the external sheath taper 158 to be inserted within the patient 15.

FIG. 32 is a side sectional view illustrating the improved obturator 240 and the improved sheath 250 dilating the incision 16. The sheath passage 254 of the improved sheath 250 and the internal passage 244 of the improved obturator 240 are threaded on the guide wire 30 and move along the flexible guide wire 30 into the vein 18 of the patient 15 by the flexible guide wire 30.

FIG. 33 is a side sectional view illustrating the removal of the flexible guide wire 30. Relative rotation between improved obturator 240 and the improved sheath 250 causes threaded engagement between the threads 264 defined on the first and second boss portions 271A and 272B and the hub threads 249.

The threaded engagement between the threads 264 defined on the first and second boss portions 271A and 272B and the hub threads 249 advances the improved obturator 240 relative to the improved sheath 250 for fracturing the endwall 253 of the improved sheath 250. The external obturator taper 246 of the improved obturator 240 fractures the sheath endwall 253 upon advancement of the improved obturator 240 relative to the improved sheath 250.

FIG. 34 is a side sectional view of a third embodiment of an improved introducer apparatus 320 of the present invention comprising an improved obturator 340 and an improved sheath 350 dilating the original incision 16. The improved introducer apparatus 320 of the present invention enables the insertion of the improved sheath 250 into the patient 15 without the use of a coupling.

The improved obturator 340 is similar to the improved obturator 240 of FIG. 29. The obturator 340 extends between a distal obturator end 341 and proximal obturator end 342 with an internal passage 344 extending therebetween. The distal obturator end 341 of the obturator 340 has an external obturator taper 346 terminating from an external surface 347. The internal passage 344 of the obturator 340 is adapted to receive the flexible guide wire 30 shown in FIGS. 2–4. The proximal obturator end 342 of the obturator 340 supports an obturator hub 348.

The improved sheath 350 is similar to the sheath 250 of FIG. 30. The improved sheath 350 has a distal sheath end 351 and a proximal sheath end 352. The distal sheath end 351 of the sheath 350 has a sheath endwall 353 at least partially enclosing the distal sheath end 351 of the sheath 350. The improved sheath 350 has an internal bore 354 extending from the proximal sheath end 352 and terminating at the sheath endwall 353. A sheath passage 355 extends through the sheath endwall 353 of the distal sheath end 351.

The sheath endwall 353 of the distal sheath end 351 of the improved sheath 350 defines an external sheath taper 356 extending from an external surface 357 of the improved sheath 350. The sheath endwall 353 defines an internal sheath taper 358.

The improved sheath 350 is provided with a frangible region 360 including weakening or score lines 361 and 362 as set forth above with reference to the weakening or score lines 161 and 162. The improved sheath 350 is provided with a first and a second handle 370A and 370B respectively secured to first and second sheath portions 350A and 350B.

The improved obturator 340 is received within the improved sheath 350 in a close sliding engagement. The improved obturator 340 is inserted within the improved sheath 350 until the tapered distal obturator end 341 is positioned adjacent to the tapered distal sheath end 351. The positioning of the tapered distal obturator end 341 adjacent to the tapered distal sheath end 351 is accomplished by the manipulation of the improved obturator 340 and the improved sheath 350 by an operator.

FIG. 34 illustrates the improved obturator 340 and the improved sheath 350 dilating the incision 16. The sheath passage 354 of the improved sheath 350 and the internal passage 344 of the improved obturator 340 are threaded on the guide wire 30 and move along the flexible guide wire 30 into the vein 18 of the patient 15 by the flexible guide wire 30.

FIG. 35 illustrates the advancement of the improved obturator 340 relative to the improved sheath 350 for fracturing the endwall 353 of the improved sheath 350. The advancement of the improved obturator 340 relative to the improved sheath 350 may be accomplished by an operator applying a force between the hub 348 and the first handle and second handle 370A and 370B. The external obturator taper 346 of the improved obturator 340 fractures the sheath endwall 353 upon advancement of the improved obturator 340 relative to the improved sheath 350.

The present invention provides an improved apparatus for inserting a medical device into a patient which overcomes the disadvantages of the inherent problems of the prior art. The improved apparatus has a smooth outer surface thereby eliminating the problems associated with the step or shoulder formed at the juncture of the dilator and the sheath of the prior art devices. The present invention provides the same ease and use as found in the prior art devices and may be provided at substantially the same or a reduced cost from the prior art devices.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An apparatus for inserting a medical device into a patient, comprising:

an obturator defining a distal obturator end;

a sheath having an internal bore terminating at a distal sheath end;

said internal bore of said sheath receiving said obturator with said obturator supporting said sheath for enabling said sheath to be inserted within the patient;

said obturator being advanceable relative to said sheath to fracture said distal sheath end;

said obturator being removable from said sheath for enabling the medical device to be inserted through said sheath to enter into the patient; and said sheath being removable from the patient while the medical device remains within the patient.

2. An apparatus for inserting a medical device into a patient as set forth in claim 1, wherein said obturator is substantially rigid and said sheath being substantially flexible; and said internal bore of said sheath receiving said obturator with said substantially rigid obturator supporting said substantially flexible sheath for enabling said substantially flexible sheath to be inserted within the patient.

3. An apparatus for inserting a medical device into a patient as set forth in claim 1, wherein said obturator is substantially rigid;

said sheath being substantially flexible; and said internal bore of said sheath receiving said obturator in a sliding engagement with said substantially rigid obturator supporting said substantially flexible sheath for enabling said substantially flexible sheath to be inserted within the patient.

4. An apparatus for inserting a medical device into a patient as set forth in claim 1, wherein said obturator extends between said distal obturator end and a proximal obturator end with said distal obturator end having a taper;

said sheath extending between said distal sheath end and a proximal sheath end with said distal sheath end having a taper; and said tapered distal obturator end of said obturator cooperating with said tapered distal sheath end of said sheath for enabling said tapered distal sheath end of said sheath to be inserted within the patient.

5. An apparatus for inserting a medical device into a patient as set forth in claim 1, wherein said obturator extends between said distal obturator end and a proximal obturator end with said distal obturator end having an external obturator taper;

said sheath extending between said distal sheath end and a proximal sheath end;

said distal sheath end having an internal sheath taper and an external sheath taper; and said internal sheath taper of said distal sheath end conforming to said external obturator taper for supporting said distal sheath end for enabling said external sheath end to be inserted within the patient.

6. An apparatus for inserting a medical device into a patient as set forth in claim 1, wherein said obturator extends between said distal obturator end and a proximal obturator end with said distal obturator end having an external obturator taper;

said sheath extending between said distal sheath end and a proximal sheath end;

said distal sheath end having a sheath endwall defining an internal sheath taper and an external sheath taper;

said internal sheath taper of said distal sheath end conforming to said external obturator taper for supporting said distal sheath end for enabling said external sheath end to be inserted within the patient; and said external obturator taper of said obturator fracturing said sheath endwall upon advancement of said obturator relative to said sheath.

7. An apparatus for inserting a medical device into a patient as set forth in claim 1, including a hub assembly for attaching said obturator relative to said sheath to enable said sheath to be inserted within the patient.

8. An apparatus for inserting a medical device into a patient as set forth in claim 1, including a hub assembly for attaching said obturator relative to said sheath to enable said sheath to be inserted within the patient; and said hub assembly detaching said obturator relative to said sheath for permitting advancement of said obturator relative to said sheath to fracture said distal sheath end.

9. An apparatus for inserting a medical device into a patient as set forth in claim 1, including a frangible region defined in said sheath for enabling said sheath to be removed from the patient and from the medical device while the medical device remains within the patient.

10. An apparatus for inserting a medical device into a patient, comprising:

a substantially rigid obturator extending between a distal obturator end and a proximal obturator end with said distal obturator end having an external obturator taper;

a substantially flexible sheath extending between a distal sheath end and a proximal sheath end with said distal sheath end having a sheath endwall defining an external sheath taper;

said sheath having an internal bore for receiving said obturator in a sliding engagement with said substantially rigid obturator supporting said substantially flexible sheath;

a hub assembly for attaching said obturator relative to said sheath for positioning said tapered distal obturator end adjacent to said tapered distal sheath end for enabling said substantially flexible sheath supported by said substantially rigid obturator to be inserted within the patient;

said hub assembly detaching said obturator relative to said sheath for permitting advancement of said obturator relative to said sheath to fracture said distal sheath end;

said obturator being removable from said sheath for enabling the medical device to be inserted through said sheath to exit from said fractured distal sheath end to enter into the patient; and a frangible region defined in said sheath for enabling said sheath to be removed from the patient and from the medical device while the medical device remains within the patient.

11. An apparatus for inserting a medical device into a patient as set forth in claim 10, wherein said sheath endwall defines an internal sheath taper and an external sheath taper; and said internal sheath taper of said distal sheath end conforming to said external obturator taper for supporting said distal sheath end for enabling said external sheath end to be inserted within the patient.

12. An apparatus for inserting a medical device into a patient as set forth in claim 10, wherein said sheath endwall defines an internal sheath taper and an external sheath taper;

said internal sheath taper of said distal sheath end conforming to said external obturator taper for supporting said distal sheath end for enabling said external sheath end to be inserted within the patient; and said external obturator taper of said obturator fracturing said sheath endwall upon advancement of said obturator relative to said sheath.

13. An apparatus for inserting a medical device into a patient as set forth in claim 10, wherein said hub assembly attaches said obturator relative to said proximal sheath end of said sheath for positioning said tapered distal obturator end adjacent to said tapered distal sheath end for enabling said substantially flexible sheath supported by said substantially rigid obturator to be inserted within the patient.

14. An apparatus for inserting a medical device into a patient as set forth in claim 10, wherein said hub assembly detaches said obturator relative to said proximal sheath end of said sheath for permitting limited advancement of said obturator relative to said sheath to fracture said distal sheath end.

15. An apparatus for inserting a medical device into a patient as set forth in claim 10, wherein said hub assembly includes a coupling for attaching said obturator relative to said sheath to position said tapered distal obturator end adjacent to said tapered distal sheath end;

said coupling being removable for permitting only a limited advancement of said obturator relative to said sheath to fracture said distal sheath end upon said limited advancement of said obturator relative to said sheath.

16. An apparatus for inserting a medical device into a patient as set forth in claim 10, wherein said hub assembly includes a threaded member for attaching said obturator relative to said sheath to position said tapered distal obturator end adjacent to said tapered distal sheath end; and said threaded member permitting limited advancement of said obturator relative to said sheath to fracture said distal sheath end upon said limited advancement of said obturator relative to said sheath.

17. An apparatus for inserting a medical device into a patient as set forth in claim 10, wherein said frangible region extends to said external sheath taper; and said frangible region facilitating the fracturing of said distal sheath end upon the advancement of said obturator relative to said sheath.

18. An apparatus for inserting a medical device into a patient as set forth in claim 10, wherein said frangible region includes a frangible line extending along said substantially flexible sheath for enabling said sheath to be removed from the patient and from the medical device.

19. An apparatus for inserting a medical device into a patient as set forth in claim 10, wherein said frangible region includes a first and a second frangible line extending along said substantially flexible sheath for enabling said sheath to be peeled away from the medical device and to be moved from the patient and from the medical device while the medical device remains within the patient.

20. An apparatus for inserting a medical device into a patient, comprising:

an obturator defining a distal obturator end;

a sheath having an internal bore terminating at a substantially closed distal sheath end;

said internal bore of said sheath receiving said obturator with said obturator supporting said sheath for enabling said sheath to be inserted within the patient;

said obturator being advanceable relative to said sheath to open said substantially closed distal sheath end;

said obturator being removable from said sheath for enabling the medical device to be inserted through said sheath to enter into the patient; and said sheath being removable from the patient while the medical device remains within the patient.

* * * * *